US009649337B2

(12) United States Patent
Rzigalinski et al.

(10) Patent No.: US 9,649,337 B2
(45) Date of Patent: May 16, 2017

(54) CERIUM OXIDE NANOPARTICLES FOR THE TREATMENT AND PREVENTION OF STROKE AND CARDIOVASCULAR DISEASE

(71) Applicants: Beverly A. Rzigalinski, Radford, VA (US); Kevin Hockey, Radford, VA (US); Landon M. Klein, Blacksburg, VA (US); Christopher A. Sholar, Rocky Point, NC (US); Justin Himler, Uniontown, OH (US); Marc J. Billings, Roanoke, VA (US); Jayce Cook, Yanceyville, NC (US)

(72) Inventors: Beverly A. Rzigalinski, Radford, VA (US); Kevin Hockey, Radford, VA (US); Landon M. Klein, Blacksburg, VA (US); Christopher A. Sholar, Rocky Point, NC (US); Justin Himler, Uniontown, OH (US); Marc J. Billings, Roanoke, VA (US); Jayce Cook, Yanceyville, NC (US)

(73) Assignee: EDWARD VIA VIRGINIA COLLEGE OF OSTEOPATHIC MEDICINE, Blacksburg, VA (US)

( * ) Notice: Subject to any disclaimer, the term of this patent is extended or adjusted under 35 U.S.C. 154(b) by 53 days.

(21) Appl. No.: 13/744,815

(22) Filed: Jan. 18, 2013

(65) Prior Publication Data
US 2014/0030335 A1 Jan. 30, 2014
US 2016/0206652 A9 Jul. 21, 2016

Related U.S. Application Data

(63) Continuation-in-part of application No. 13/539,564, filed on Jul. 2, 2012, now Pat. No. 8,747,907, which is a continuation of application No. 11/993,260, filed as application No. PCT/US2006/024963 on Jun. 27, 2006, now abandoned.

(60) Provisional application No. 61/587,818, filed on Jan. 18, 2012, provisional application No. 60/693,930, filed on Jun. 27, 2005.

(51) Int. Cl.
A61K 33/24 (2006.01)
(52) U.S. Cl.
CPC .................. A61K 33/24 (2013.01)
(58) Field of Classification Search
None
See application file for complete search history.

(56) References Cited

U.S. PATENT DOCUMENTS

| 5,460,701 | A | 10/1995 | Parker et al. |
| 5,514,349 | A | 5/1996 | Parker et al. |
| 5,874,684 | A | 2/1999 | Parker et al. |
| 6,669,823 | B1 | 12/2003 | Sarkas et al. |
| 7,347,987 | B2 | 3/2008 | McGinnis et al. |
| 7,534,453 | B1 * | 5/2009 | Rzigalinski et al. ......... 424/617 |
| 2003/0231992 | A1 | 12/2003 | Sarkas et al. |
| 2006/0246152 | A1 | 11/2006 | McGinnis et al. |
| 2009/0092671 | A1 | 4/2009 | Rzigalinski et al. |
| 2010/0098768 | A1 * | 4/2010 | Andreescu et al. .......... 424/489 |
| 2010/0166821 | A1 | 7/2010 | Rzigalinski et al. |
| 2012/0070500 | A1 * | 3/2012 | Cimini et al. ................ 424/490 |
| 2013/0004584 | A1 | 1/2013 | Rzigalinski et al. |

FOREIGN PATENT DOCUMENTS

| WO | 9503907 A1 | 2/1995 |
| WO | 2007002662 A2 | 1/2007 |

OTHER PUBLICATIONS

Rzigalinski et al., "Cerium oxide nanoparticles increase the lifespan of cultured brain cells and protect against free radical and mechanical trauma", Abstract #377.24, 2003 Experimental Biology meeting abstracts.
Abney, Barb, "UCF brain cell research spawns hope for longer life", Univ. of Central Florida, Aug. 13, 2003, p. 1 of 1, http://www.eurekalert.org/pub_releases/2003-08/uocf-ubc081303.php.
Szilagyi, et al., "Visualization of mitochondrial membrane potential and reactive oxygen species via double straining", Neuroscience Letters, Limerick, IE, vol. 399, No. 3, May 22, 2006, pp. 206-209.
Weber, et al., Traumatic Injury of Cortical Neurons Causes Changes in Intracellular Calcium Stores and Capacitative Calcium Influx, Jnl of Biological Chemistry, 2001, vol. 276, No. 3, Issue of JAN 19, pp. 1800-1807.
Rzigalinski et al., "Calcium Influx Factor, Further Evidence it is 5, 6-Epoxyeicosatrienoic Acid", Jnl of Biological Chemistry, vol. 274, No. 1 Issue of JAN 1, pp. 175-182, 1999.
Zhang, et al. "Reduction of Voltage-Dependent Mg2+ Blockade of NMDA Current in Mechanically Injured Neurons", Science, vol. 274, Dec. 13, 1996.
Clark et al. "Engineered oxide nanoparticles increase neuronal lifespan in culture and act as free radical scavengers", Society for Neuroscience, Abstract: 2000-2005.
Schubert et al., "Cerium and yttrium oxide nanoparticles are neuroprotective", Biochemical and Biophysical Research Communications, 342, 2006.
Strawn E.T. et al., Cerium oxide nanoparticles increase lifespan and protect against free radical medicated toxicity, FASEB Journal, vol. 20, No. 5, part 2, Mar. 2006, pp. A1356.
Callaghan P.G. et al., "Deleterious effects of microglia activated by in vitro trauma are blocked by engineered oxide nanoparticles," Society for Neuroscience Abstract Viewer and Itinerary Planner, vol. 2003, Abstract No. 11.7, 33rd Annual Meeting of the Society of Neuroscience, New Orleans, LA, Nov. 8-12, 2003.
Dacey, "Dopamine-Accumulating retinal neurons revealed by in vitro fluorescence display a unique morphology", Science, vol. 240, pp. 1196-1198, 1988.

(Continued)

Primary Examiner — Robert A Wax
Assistant Examiner — Danah Al-Awadi
(74) Attorney, Agent, or Firm — Tarolli, Sundheim, Covell & Tummino LLP

(57) ABSTRACT

A method of treating or preventing neurological injury in a subject who has suffered a stroke is described. The method includes administering a therapeutically effective amount of cerium oxide nanoparticles to the subject. Methods for prophylaxis against neurological injury from stroke, and methods for treating or preventing cardiovascular disease by administration of a therapeutically effective amount of cerium oxide nanoparticles are also described.

14 Claims, 12 Drawing Sheets

(56) References Cited

OTHER PUBLICATIONS

Clark A. et al., "Engineered oxide nanoparticles increase neuronal lifespan in culture and act as free radical scavengers", Society for Neuroscience Abstract Viewer and Itinerary Planner, vol. 2003, 33rd Annual Meeting of the Society of Neuroscience, New Orleans, LA, Nov. 8-12, 2003.
European Extended Search Report; European patent application 06785640.1-2123.
PCT Search Report and Written Opinion; PCT/US2006/024963.
Chinopoulos et al., "Mitochondria deficient in complex I activity are depolarized by hydrogen peroxide in nerve terminals: relevance to Parkinson's disease", Jnl of Neurochemistry, vol. 76, pp. 302-306, 2001.
Rzigalinski, B.A., "Nanoparticles and cell longevity", Technology in Cancer research & Treatment, vol. 4, No. 6, Dec. 2005, pp. 651-659.
Cook et al., "Neuronal damage induced by polychlorinated biphenyls is partially reversed by cerium oxide nanoparticles", Annual Meeting of the Society of Neuroscience, vol. 2003, Jan. 1, 2003, Abstract No. 669.13.
Thompson, "Nanoparticles Pop Up Everywhere", Discover Magazine, Jan. 2004 Issue, http://discovermagazine.com/2004/jan/technology.
Rzigalinski et al., "Antioxidant Nanoparticles", Nanomedicine in Health and Disease, CRC Press, NY, 2011, pp. 102-121.
Cohen et al., "Radical Nanomedicine", Nanomedicine, Dec. 2006, pp. 1-13.
Kumar, "Tissue, Cell and Organ Engineering ", Nanotechnologies for the Life Sciences, Book 4, Jan. 1, 2007.
Nanotech Conference & Expo 2011 "Nanotechnology 2011: Bio Sensors, Instruments, Medical, Environment and Energy" NSTI-Nanotech 2011, vol. 3.
Rzigalinski et al., "Antioxidant Nanoparticles" Nanomedicine in Health and Disease, pp. 100-121.
Rzigalinski et al., "Cell Biology and Metabolism: Calcium Influx Factor, Further Evidence It is 5,6-Epoxyeicosatrienoic Acid" The Journal of Biological Chemistry, 1999, 274, pp. 175-182.
Weber et al., "Mechanisms of Signal Transduction: Traumatic Injury of Cortical Neurons Causes Changes in Intracellular Calcium Stores and Capacitative Calcium Influx", The Journal of Biological Chemistry, 2001, 276, pp. 1800-1807.
Zhang et al., "Reduction of Voltage-Dependent Mg2+ Blockade of NMDA Current in Mechanically Injured Neurons", Science, Dec. 13, 1996, vol. 274, pp. 1921-1923.

\* cited by examiner

CERIUM OXIDE NANOPARTICLES FOR THE TREATMENT AND PREVENTION OF STROKE AND CARDIOVASCULAR DISEASE

CROSS-REFERENCE TO RELATED APPLICATIONS

This application claims priority to U.S. Provisional Patent Application 61/587,818 and US patent application Ser. No. 13/539,564; filed on Jul. 2, 2012, which is a continuation of U.S. patent application Ser. No. 11/993,260, filed Dec. 20, 2007, which is a U.S. National Stage Application of PCT/US2006/024963, filed Jun. 27, 2006, which claims priority to U.S. Provisional Patent Application Ser. No. 60/693,930, filed Jun. 27, 2005, all of which are incorporated herein by reference in their entirety.

GOVERNMENT FUNDING

This invention was made partially with U.S. Government support from the United States National Institutes of Health under Contract No. NS40490 (National Institute of Neurological Disorders & Stroke) and AG022617 (National Institute on Aging). The U.S. Government has certain rights in the invention.

BACKGROUND

Field of the Invention

The present invention relates to the field of medicine. More specifically, the invention relates to compositions containing cerium oxide nanoparticles for the treatment and prevention of stroke and cardiovascular disease.

Description of the Related Art

Many approaches have been taken to treat, either therapeutically or prophylactically, diseases, disorders, and other medically important conditions that have, as a major component, cell injury or death due to free radicals, such as oxygen radicals. Among those approaches were the use of free radical scavengers, such as Vitamin E and its related compounds, Vitamin C and its related compounds, and melatonin, to name a few. While the beneficial effects of these compounds have been noted, researchers and clinicians continue to search for compounds with higher activities and half-lives.

In early experiments performed by the present inventors and their colleagues, cerium oxide nanoparticles prepared by a sol-gel process were utilized to enhance cell longevity. The cerium oxide nanoparticles were proposed to act as free radical scavengers to bring about the observed results. However, the sol-gel process posed several difficulties. For example, particle size was not well-controlled within the reported 2-10 nm range, making variability between batches high. That is, the process, while satisfactory for producing nanoparticles with free radical scavenging activity, did not reproducibly produce particles of a specific size range. Thus, each batch of particles needed to be tested to confirm the size range and the suitability of the batch for use. In addition, the process resulted in tailing of surfactants used in the process into the final product. The presence of these surfactants produced biological difficulties when used, primarily due to the toxicity of the surfactants in the product. Furthermore, the inability to control the amount of surfactant tailing posed problems with agglomeration when nanoparticles were placed in biological media. These difficulties reduced particle efficacy and biological deliverability. Removal of surfactant after sol-gel synthesis produced particles that appeared prone to agglomeration in biological media, and had a lack of biological effects. Further, difficulties were encountered with changes in valence state of cerium associated with these particles, causing alterations in the ratio of valence states of cerium (+3/+4) that occurred over time, particularly when particles were placed in biological media. It is possible that the +3/+4 ratio of valence states in the nanoparticles might alter free radical scavenging and cellular delivery, including delivery in vivo.

Damage from ischemic stroke results from generation of free radicals in neurons and other brain cells, which cause in cellular demise and loss of function. Loss of energy production due to damaged mitochondria is also evident. Depending on the size and location of the stroke, functional deficits can range from mild loss of coordination and limb movement to coma.

It has been shown that cerium oxide nanoparticles (CeONP) are potent and effective regenerative free radical scavengers and mitochondrial protectants (Bailey et al., Nature Biotechnology 14, 112 (2003); Rzigalinski et al., Nanomedicine, 1: 399-412 (2006); Rzigalinski et al., Antioxidant Nanoparticles in Nanomedicine in Health and Disease, Science Publishers, 2012). It has also been shown that CeONP show promise in treatment of traumatic brain injury (Whiting et al., J. Neurotrauma 26, 101 (2009)) and Parkinson's Disease (Dillon et al., "Cerium oxide nanoparticles protect against MPTP-induced dopaminergic neurodegeneration in a mouse model for Parkinson's Disease" Proc. of International Conf. on Nanotechnology, in press), and other neurodegenerative disorders. However, the use of cerium oxide nanoparticles for the treatment of stroke has not been previously demonstrated.

SUMMARY

The present invention addresses the need for treatments to improve recovery after stroke or cardiovascular disease by providing compositions and methods for treating and/or preventing stroke and cardiovascular disease, and for improving neuronal and cardiovascular recovery after stroke and cardiovascular disease.

The inventors have demonstrated that cerium oxide nanoparticles can be formulated as nanopharmaceuticals that can be used in the treatment of stroke and cardiovascular disease. The data presented herein shows that, in a tissue culture model of stroke (anoxia), treatment with cerium oxide nanoparticles improved neuronal survival by 78% and maintained normal mitochondrial membrane potential and calcium signaling. Further, treatment of cells up to eight (8) hours post anoxia improved survival and cellular function as compared to untreated cells. In a *Drosophila* model of stroke, cerium oxide nanoparticles improved survival by 30% and allowed flies subjected to stroke to maintain better motor function and climbing ability than untreated controls. The results show that cerium oxide nanoparticles can be used for the treatment and prevention of stroke and cardiovascular disease.

The invention thus provides compositions comprising cerium oxide nanoparticles for the treatment of stroke, cardiovascular disease, or both. It likewise provides compositions comprising cerium oxide nanoparticles for the prevention of stroke, cardiovascular disease, or both.

In one aspect, the present invention provides a method of treating or preventing neurological injury in a subject who has suffered a stroke that includes administering a therapeutically effective amount of cerium oxide nanoparticles to the subject. In another aspect, a method of providing prophylactic protection from neurological injury in a subject is provided that includes administering a therapeutically effective amount of cerium oxide nanoparticles to the subject. In a further aspect, a method of treating or preventing cardiovascular disease in a subject is provided that includes administering a therapeutically effective amount of cerium oxide nanoparticles to the subject. In some embodiments, the cardiovascular disease is ischemic heart disease.

DETAILED DESCRIPTION

Figure 1:
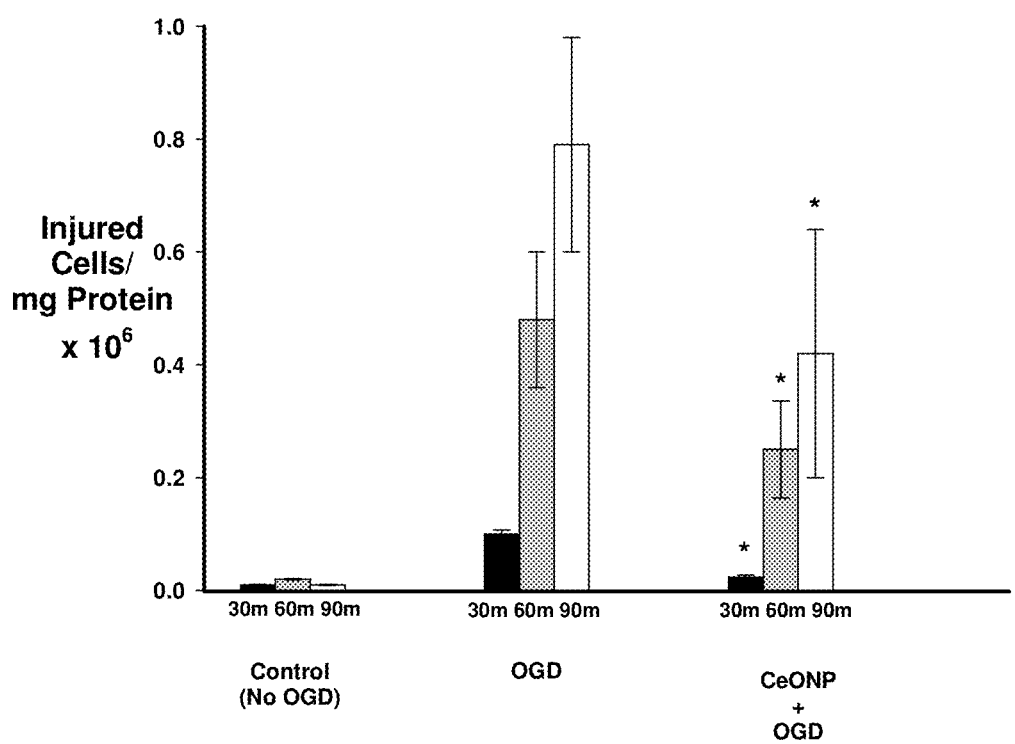
FIG. 1 provides a bar graph showing that Cerium Oxide Nanoparticles protect neurons of mixed organotypic cultures from cell damage associated with oxygen/glucose deprivation. Mixed organotypic brain cell cultures (15 days old) were treated with a single dose of 100 nM cerium oxide nanoparticles on day 5 in vitro. On day 15, cultures were exposed to oxygen/glucose deprivation for 30, 60, or 90 minutes as indicated in the figure, followed by return to normal culture conditions for 24 hours. At this time, cell death/damage was measured by uptake of Propidium iodide, expressed on the Y axis as "injured cells per mg of protein". *Significantly different from OGD, P<0.01.

Unless otherwise defined, all technical and scientific terms used herein have the same meaning as commonly understood by one of ordinary skill in the art to which this application pertains. Although methods and materials similar or equivalent to those described herein can be used in the practice or testing of the exemplary embodiments, suitable methods and materials are described below. In case of conflict, the present specification, including definitions, will control. In addition, the materials, methods, and examples are illustrative only and not intended to be limiting.

DEFINITIONS

The terminology as set forth herein is for description of the embodiments only and should not be construed as limiting the application as a whole. Unless otherwise specified, "a," "an," "the," and "at least one" are used interchangeably. Furthermore, as used in the description of the application and the appended claims, the singular forms "a", "an", and "the" are inclusive of their plural forms, unless contraindicated by the context surrounding such.

The recitations of numerical ranges by endpoints include all numbers subsumed within that range (e.g., 1 to 5 includes 1, 1.5, 2, 2.75, 3, 3.80, 4, 5, etc.).

The expression "therapeutically effective amount" as used herein, refers to a sufficient amount of agent to exhibit a therapeutic effect. The exact amount required will vary from subject to subject, depending on the species, age, and general condition of the subject, the particular therapeutic agent, its mode and/or route of administration, and the like. It will be understood, however, that the total daily usage of the compounds and compositions of the present invention can be decided by an attending physician within the scope of sound medical judgment. The specific therapeutically effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific composition employed; the duration of the treatment; drugs used in combination or coincidental with the specific composition employed; and like factors well known in the medical arts.

Treatment, as used herein, encompasses the administration of cerium oxide nanoparticles to a subject that has already suffered symptoms of a disease. In some embodiments, treatment is effective to eliminate the disease and/or its symptoms; in another embodiment, administration of the cerium oxide nanoparticles is effective to decrease the severity of the disease and/or its symptoms. Treatment includes improvement in the condition through lessening or suppression of at least one symptom and/or delaying in progression of the disease. Preventing, as used herein, refers to avoiding the development of additional symptoms or the development of a more severe case of a disease.

To address the shortcomings of prior attempts to develop cerium oxide nanoparticles for use in treating damage caused by free radicals, different methods of synthesizing nanoparticles, and thus different nanoparticles, were investigated. Efforts were directed toward examining the biological efficacy of commercially available cerium oxide nanoparticles prepared by existing manufacturing processes. These included cerium oxide nanoparticles available from Nanophase Technologies Corporation (Romeoville, Ill.), Advanced Powder Technology Pty Ltd. (Welshpool, Western Australia), and NanoScale Materials Inc. (Manhattan, Kans.). In summary, in a series of experiments, it was found that cerium oxide nanoparticles produced by Nanophase Technology Corporation, using specific, patented mechanisms of synthesis, provided consistently reproducibly sized nanoparticles that consistently showed high levels of biological activity. With sizes of 20 nm and below, particles readily entered cells and reduced free-radical mediated damage. Synthesis for these particles has been described in the following patents, the disclosures of the entireties of all of which are incorporated herein by reference: U.S. Pat. No. 6,669,823, U.S. Pat. No. 5,460,701, U.S. Pat. No. 5,514,349, U.S. Pat. No. 5,874,684, Japanese Patents JP2980987 and JP3383608, European Patent EP0711217B1, German Patent DE69426886, French Patent FR94922757, Great Britain Patent GB94922757, and Australian Patent AU068582882.

It was surprisingly found that the new source of cerium oxide nanoparticles provided superior reproducibility of activity from batch to batch, and showed lower toxicity to mammalian cells. It was determined that the cerium oxide nanoparticles used in the present invention were different from the prior nanoparticles in quality and size distribution, factors that significantly contribute to their improved characteristics in treating subjects according to the methods of the invention. In developing the invention, it was determined that, regardless of source, cerium oxide particles having a small size, narrow size distribution, and low agglomeration rate are most advantageous. Also, for delivery, the nanoparticles are advantageously in a non-agglomerated form. To accomplish this, stock solutions of about 10% by weight can be sonicated in ultra-high purity water (16 megaohms). These nanoparticles are superior to previously developed cerium oxide nanoparticles for treatment of and protection against, damage caused by free radicals. This new and useful improvement allows cerium oxide nanoparticles to be used in extending the life of a cell in vivo as well as in vitro. In particular, it is shown herein the novel finding that cerium oxide nanoparticles of a defined size range and distribution and made by a method other than sol-gel synthesis increase the lifespan of cells, such as cells of an organism in vivo. Also shown is that cerium oxide nanoparticles enhance the lifespan of mammalian cells in culture and in vivo, act as potent free radical scavengers, and possess significant anti-inflammatory and radioprotective properties in vivo.

While not wishing to be limited to any single method of action, it is thought that cerium oxide nanoparticles have a unique oxide lattice and valence structure that might confer them with the ability to scavenge (detoxify) intracellular free radicals, and might thus convey their anti-inflammatory, radioprotective, and longevity-enhancing properties. Further, the data obtained by the inventors, and provided herein, suggests that the valence and oxygen lattice structure conveys the ability of cerium oxide nanoparticles to regenerate a biologically active matrix after a free radical scavenging event. This allows small, single doses of nanoparticles to remain active within the cell for long periods of time, conveying regenerative biological effects. In contrast, most commonly available free radical scavengers, such as vitamin E, nitrosone compounds, and vitamin C are inactivated by alteration of their chemical structure after scavenging a single free radical. This loss of structure limits their pharmacological efficacy and requires high dosing regimens.

It appears that the regenerative activity of the cerium oxide nanoparticles may be dependent on a well-known oscillating chemical phenomenon, known as the Belousov-Zhabotinsky (B-Z) reaction, in which cerium oxide serves to facilitate oscillation of electrons (or free radicals) from one compound to another. Cerium in the nanoparticles exists in two valence states, +3 and +4. Adequate propagation of B-Z requires a specific ratio of Ce+3 to +4 in the nanoparticles. If the composition changes to have too much +3 cerium, the reaction will not propagate. Research has shown that as the cerium oxide nanoparticle size is reduced from 30 nm to 3 nm, lattice strain in the nanoparticles causes more cerium to be in the +3 state. Although this mechanism has only been studied in vitro up to now, this mechanism of action may also be true in vivo and would provide a significant advantage to using larger sizes of cerium oxide nanoparticles.

Further research has also shown that cerium oxide nanoparticles have a beneficial effect on mitochondrial dysfunction which may also contribute to their beneficial effects in treating stroke and cardiovascular disease. The inventors have shown that cerium oxide nanoparticles enter the mitochondria, and can substitute for damaged elements of the electron transport change, thereby improving ATP synthesis and mitochondrial membrane potential in diseases, such as stroke, in which mitochondrial damage is evident. As such, cerium oxide nanoparticles replace damaged semiconductor elements of cellular mitochondria and improve energy production in disease and damaged tissue. Further discussion of the role of cerium oxide nanoparticles in treating mitochondrial dysfunction can be found in U.S. patent pplication Ser. No. 12/252,905 (Rzigalinski et al.), the disclosure of which is incorporated herein by reference.

Broadly speaking, the present invention provides a method of treating at least one cell with cerium oxide particles. The method generally comprises contacting at least one cell with an amount of cerium oxide nanoparticles that reduces or eliminates damage caused by free radicals, which are unstable, highly reactive molecules such as nitric oxide, superoxide, hydroxyl radicals, peroxynitrite, and other unstable reactive compound formed from the above. They cause aging and various diseases by taking electrons from other molecules in the body, a process that causes cell or oxidative damage. As used herein, cell or oxidative damage has the same meaning as oxidative stress.

"Contacting" means any action that results in at least one cerium oxide nanoparticle physically contacting at least one cell. It thus may comprise exposing the cell(s) to cerium oxide nanoparticles in an amount sufficient to result in contact of at least one cerium oxide nanoparticle with at least one cell. The method can be practiced in vivo, in which case contacting means exposing at least one cell in a subject to at least one cerium oxide nanoparticle. According to the invention, contacting thus may comprise exposing at least one cell to at least one cerium oxide particles, such as, for example by administering cerium oxide particles to a subject via any suitable route. It also may comprise exposing cells in vitro or ex vivo by introducing, and preferably mixing, cerium oxide particles and cells in a controlled environment, such as a culture dish or tube. Optionally, where practiced in vitro or ex vivo, some or all of the cerium oxide particles that are not taken up or adsorbed by cells are removed, for example by washing the cells in suitable media, buffer, water, etc. According to the invention, contacting may comprise introducing, exposing, etc. the cerium oxide particles at a site distant to the cells to be contacted, and allowing the bodily functions of the subject, or natural (e.g., diffusion) or man-induced (e.g., swirling) movements of fluids to result in contact of the nanoparticle(s) and cell(s). Where practiced ex vivo, the cells may also be re-introduced into a subject, preferably the subject from which they were originally obtained. In one embodiment, this includes putting the particles into a gel or other packet that limits diffusion, followed by implanting it into a body area such as a knee joint.

According to the method of the invention, the subject, individual, or patient can be any organism to whom the cerium oxide nanoparticles are administered. Thus, the subject may be a human or a non-human animal, such as another mammal, including, but not limited to a rodent (e.g., mouse, rat, rabbit), a canine (e.g., a dog), a feline (e.g., a cat), an equine (e.g., a horse), an ovine (e.g., a sheep), an orcine (e.g., a pig), or a bovine (e.g., a cow or steer). The subject can be any other animal such as a bird, reptile, amphibian, or any other companion or agricultural animal.

The method can be practiced in vivo as either a therapeutic method of treating a disease or disorder involving free radicals or as a prophylactic method to prevent free radical damage. In embodiments where the method is a method of treating (i.e., a therapeutic method), the amount is an amount that is effective for reducing or eliminating cell death or dysfunction or tissue or organ damage due to free radicals that are being produce, or were produced previously, in the subject, or mitochondrial damage produced by stroke or cardiovascular disease. The subject, individual, or patient may be one who is in immediate or apparent need of, or suspected of being in need of, treatment for a disease or disorder associated with free radicals, or it may be one who is in immediate or apparent need of, or suspected of being in need of, treatment for an injury or other trauma resulting from or known to result in production of free radicals. In such situations, where a pre-existing condition related to cell, tissue, or organ damage due to free radicals is evident or suspected, the method is a therapeutic method. For example, if a subject has had a stroke, it may be beneficial to treat the subject with cerium oxide nanoparticles to reduce the effects of the stroke.

In addition, according to the methods of the invention, the subject, individual, or patient may be one who is not in or suspected of being in need of treatment of a pre-existing disease, disorder, or injury or trauma. In such situations, the method is a prophylactic method. Prophylactic methods are useful in situations where the subject is currently engaged in, or soon to be engaged in, one or more activities that might result in an injury or trauma. They are also useful in situations where the patient has a likelihood of developing a disease or disorder associated with cell, tissue, or organ damage due to free radicals. Thus, the present methods are useful not only for treating patients with a disease or disorder, but for treating patients who are suspected of having a predisposition to a disease or disorder. For example, if the family of a subject has been shown to be prone to a certain neurodegenerative disease, the subject may be given cerium oxide nanoparticles to avoid or reduce the effects of that disease. Likewise, if a subject exhibits one or more risk factors associated with stroke, it may be beneficial to prophylactically administer cerium oxide nanoparticles to decrease the amount of neurological damage that may result should a stroke occur.

As another example to compare prophylactic and therapeutic methods, in embodiments where the method is a prophylactic method, the amount is an amount that is effective in reducing or blocking cell death or dysfunction or tissue or organ damage due to free radicals that might be produced in the subject in the future. For example, in a therapeutic method, the cerium oxide nanoparticles may be administered to a patient following a head injury to reduce the amount of damage to the brain as a result of the injury. In contrast, in a prophylactic method, the cerium oxide nanoparticles may be administered to a subject prior to engaging in an activity that has a likelihood of head injury, such as a car race or other high-speed activity.

The act of administering cerium oxide nanoparticles can be any act that provides the cerium oxide nanoparticles to a subject such that the particles can function for their intended purpose. For example, administering can be by injection or infusion. It can thus be an intramuscular, intraperitoneal, subcutaneous, or intrathecal injection, or a slow-drip or bolus infusion. Other non-limiting examples of methods of administration include topical administration, such as by way of lotions, salves, or bandages, often on intact skin but also through open wounds, lesions, or sores. Yet other non-limiting examples include administration through mucous membranes, such as by way of intranasal administration through inhalation of dry particles or a mist comprising the particles, oral ingestion, sublingual absorption, by subcutaneous means, and rectal or vaginal delivery. The vehicle of delivery may be in any suitable form, such as the form of an oral solution, gel, tablet, capsule, powder, suppository, infusible, lozenge, cream, lotion, salve, inhalant, or injection.

According to embodiments of the method, the method can comprise repeating the act of contacting (e.g., administering) the cerium oxide nanoparticles. In embodiments relating to administering the cerium oxide to subjects, repeating the administration can include one or more administrations in addition to the original administration. The amount to be administered to each subject will vary depending on usual factors taken into consideration for dosing of pharmaceuticals, such as weight, general health, and metabolic activities of the patient. Likewise, the mode of administration (e.g., injection, oral administration) will be taken into account when determining the proper amount of nanoparticles to administer per dose.

In general, a dosing of about 0.005 to about 500 micrograms per gram of body weight, with doses in the range of about 0.05 micrograms to about 50 micrograms per gram of body weight of 10-20 nm cerium oxide nanoparticles being more preferred. Specific embodiments may use about 50 ng, 100 ng, 500 ng, 1 µg, 5 µg, 10 µg, or 50 µg per administration or per gram body mass per administration should be effective in providing the desired therapeutic or prophylactic result. Of course, injection or infusion amounts will tend to be on the lower end of the range while oral administration amounts will tend to be on the upper end. Current results suggest that the optimal dose for 10-20 nm cerium oxide nanoparticles is 10 nM to 1 uM for blood and intracellular fluid levels. However, the action of the particles is highly dependent on other variables and so these amounts will vary depending on the surface area, the species of the subject, the reason for administration, etc. Amounts may be higher when the method is practiced in vitro or ex vivo because excess particles may be easily removed at any time by washing, etc.

It should be noted that this method shows low toxicity in mammalian cells, fruit flies, rats, and mice, and thus is expected to show low toxicity in other animal cells. This new and useful improvement allows the method of the present invention to be used in subjects with lower toxicity than in previous inventions. This important feature of the present invention means that the cerium oxide nanoparticles can be used in a broad range of applications. In preferred embodiments, the cerium oxide nanoparticles do not contain docusate sodium, which has been shown to produce toxicity in tissue culture. Also, in preferred embodiments, there are less than 0.01% (w/w or w/v) of any other contaminating ions, metals, or other substances, which can also cause toxicity to cells.

Although the cerium oxide nanoparticles show very low toxicity, in some instances it might be desirable to provide multiple, low doses of particles to an individual. In such cases, the method may comprise two or more administrations of less than the total effective amount, where the amount ultimately administered is an effective amount. Likewise, multiple administrations of an effective dose may be desirable where the second or subsequent administration is performed at a time well separated from the first administration. That is, because the cerium oxide nanoparticles are highly stable, even after being administered, repeated administrations of effective doses are envisioned as occurring at widely spaced intervals, such as months or years apart.

The invention thus includes a method of providing prophylactic protection from neurological injury in a subject. This aspect involves administering a therapeutically effective amount of cerium oxide nanoparticles to the subject before the occurrence of stroke. Because of the high stability of cerium oxide nanoparticles, the nanoparticles can be administered well in advance of the occurrence of a stroke, with repeated administration being provided in some embodiments at widely spaced intervals. In some embodiments, the cerium oxide nanoparticles are prophylactically administered to subjects who have one or more risk factors associated with the occurrence of stroke.

Furthermore, where multiple administrations are performed, different modes of administration may be used. For example, if two doses are administered, one can be an injection whereas the other can be oral. In addition, if three or more doses are administered, two or more may be by the same mode, while the remaining may be from one or more different mode, in any combination, number, and order. Of course, where multiple administrations are used, each administration may be by a different mode. The mode of administration, the number of times it is repeated, and the sequence of modes of administration may be selected by those of skill in the art based on numerous considerations, and such selection is well within the abilities of those of skill in the art.

The method can also be practiced in vitro which means that contacting at least one cell with at least one cerium oxide nanoparticle can occur in a petri dish, a test tube, an IV tube, or any other container applicable for contacting. When practiced in vitro, it may be a method for identifying parameters that are useful in in vivo treatment regimens. The method can be practiced to study the effects of combinations of nanoparticles with drugs on cells. For example, the cerium oxide nanoparticles can be combined with other known antioxidants such as vitamin E, n-acetyl cysteine, or melatonin. The cerium oxide nanoparticles could also be combined with disease specific drugs. The in vitro methods can also comprise using the cerium oxide nanoparticles as a research tool to observe the effects of free radicals on cells or observe the cells for changes in protein expression, cell morphology, or any other characteristic of interest.

In preferred embodiments, the method is practiced with size-limited cerium oxide nanoparticles made by a method other than a sol-gel method. The nanoparticles useful in the present invention have pre-defined sizes clustered tightly within a range. In general, the particles have a size of about 1 nm or less to about 500 nm. In embodiments, the particles are 11 nm or more. In embodiments where particles are taken into the interior of cells, the preferable range of particles that are taken into the cell are from about 11 nm to about 50 nm, such as about 20 nm. In embodiments where particles exert their effects on cells from outside of the cells, the preferable range of particles that are extracellular are from about 11 nm to about 500 nm. In embodiments, the particles are from about 40 nm to about 500 nm. In other embodiments, the particles are from about 11 nm to about 40 nm, such as from about 11 nm to about 20 nm, about 15 nm to about 20 nm, about 11 nm to about 15 nm, or about 30 nm to 40 nm. Of course, any specific size range within these general sizes can be provided, the size being selected by the practitioner based on any number of parameters. According to the invention, the term "about" is used to indicate a margin of error for a statistically significant portion of the particles of 10%. Thus, particles of a size of 20 nm include those in which a majority of the particles fall within the range of 18 nm to 22 nm. In embodiments, 95% of the cerium oxide nanoparticles have a size of between about 15 nm and about 25 nm. In embodiments, 95% of the cerium oxide nanoparticles are within 5% of 20 nm. In other embodiments, 90% of the cerium oxide nanoparticles have a size of between about 18 nm and about 22 nm.

In certain embodiments, the invention provides compositions comprising cerium oxide nanoparticles for improving neuronal recovery after stroke, or for treating or preventing cardiovascular disease. Cerium oxide nanoparticles having a size below 10 nm results in decreased ability to scavenge multiple types of free radicals. As size decrease, only superoxide radicals were scavenged, with less scavenging of hydroxyl and nitroxyl radicals. In stroke, as in other neurodegenerative diseases, superoxide radicals represent only a small fraction of the radicals actually produced, with hydroxyl and nitroxyl radicals being more abundant. For further discussion of the effect of particle size on the scavenging of different types of free radicals, see Rzigalinski et al., "Antioxidant Nanoparticles," Nanomedicine in Health and Disease, Hunter R. J. & Preedy, V. R. (eds.), CRC press, NY, 2011, the disclosure of which is incorporated herein by reference. Accordingly, in some embodiments, the cerium oxide nanoparticles have a size range of from about 5 nm to about 25 nm, such as from 7 nm to 20 nm, 7 nm to 12 nm, 13 nm to 20 nm, 14 nm to 20 nm, 15 nm to 20 nm. In embodiments, a majority of the particles have a size within the range of 18 nm to 22 nm. In other embodiments, the nanoparticles have an average size of about 10 nm.

The present invention provides methods of treating individuals suffering from, or suspected of suffering from, a disease or disorder involving free radicals, such as oxygen radicals, or a disease involving mitochondrial dysfunction. It likewise provides methods of treating individuals suffering from, or suspected of suffering from a complication of an injury that results from free radicals, such as oxygen radicals, or results in the production of free radicals, such as oxygen radicals. In general, the methods of the invention comprise administering to an individual (used interchangeably herein with "subject" and "patient") an amount of cerium oxide nanoparticles sufficient to reduce or eliminate cell, tissue, or organ damage in the individual that is caused by free radicals. Thus, the invention encompasses the use of cerium oxide nanoparticles in enhancement of cell and organism longevity, reduction of inflammation and inflammatory disorders, reduction in tissue damage due to inflammatory disorders, and reduction in radiation injury.

While the above disclosure discusses administration in vivo, it is important to recognize that the present invention also encompasses administering ex vivo. Thus, a method according to the invention can comprise removing at least one cell from an organism, administering cerium oxide nanoparticles to that cell, then returning the cell to its natural environment (e.g., into the body of the patient). In such situations, the act of administering can be simply exposing the nanoparticles to the cell, for example in a culture dish or a tube. In one particular embodiment, the method of ex vivo administration comprises obtaining blood from a patient, exposing the blood to cerium oxide nanoparticles, and returning the treated blood to the patient. The method can comprise separating cerium oxide nanoparticles from the blood prior to returning the blood to the patient.

In another embodiment, the present invention is used to affect, either prophylactically or therapeutically, cell longevity in organisms. The methods treat or affect, either prophylactically or therapeutically, diseases or disorders associated with free radicals, or cell death or tissue or organ damage due to free radicals. In general, the methods comprise administering to a subject an amount of cerium oxide nanoparticles sufficient to reduce, eliminate, or block cell, tissue, or organ damage caused by free radicals in the subject.

In one embodiment, the cerium oxide nanoparticles can be taken up by the cell. In this case, they can act to reduce or eliminate free radicals within the cell. This method can be used for the prevention or treatment of brain disease, spinal cord disease, or other neurological trauma. This method can also be used for the treatment or prevention of neurodegenerative disorders such as Alzheimer's disease, Parkinson's disease, Huntington's disease, amyotrophic lateral sclerosis (ALS), multiple sclerosis, toxin-mediated damage, or stroke. This method may be used in the treatment or prevention of cardiovascular disease, diabetes, diseases of the retina, asthma, respiratory dysfunctions, and allergic or autoimmune diseases, such as chronic obstructive pulmonary disease and lupus. It is to be understood that the diseases stated above are only examples and are not to be understood as limiting the invention in anyway.

A stroke is a medical condition that can cause permanent neurological damage and death. Strokes can be classified into two major categories: ischemic and hemorrhagic. Ischemic strokes are those that are caused by interruption of the blood supply, while hemorrhagic strokes are the ones which result from rupture of a blood vessel or an abnormal vascular structure In an ischemic stroke, blood supply to part of the brain is decreased as a result of thrombosis (obstruction of a blood vessel by a blood clot forming locally), embolism (obstruction due to an embolus from elsewhere in the body, see below), systemic hypoperfusion (general decrease in blood supply, e.g., in shock), or venous thrombosis. Risk factors associated with an increased likelihood of having a stroke include old age, high blood pressure, previous stroke or transient ischemic attack, diabetes, high cholesterol, tobacco smoking and atrial fibrillation.

The neurological damage caused by a stroke can result in various symptoms, such as motor function disorders and various sensory and cognitive disorders. More specifically, symptoms include numbness, altered smell, taste, hearing, or vision, drooping of eyelid, decreased reflexes (e.g., gag, swallow, pupil reactivity to light), balance problems, altered breathing and heart rate, various speech disorders such as aphasia and dysarthria, memory deficits, confusion, altered walking gait, and lack of movement coordination.

One embodiment of the invention provides a method of treating or preventing neurological injury in a subject who has suffered a stroke by administering a therapeutically effective amount of cerium oxide nanoparticles to the subject. As described, the neurological injury from a stroke results from a disruption in the blood supply, resulting in cell death due in part to free radical formation. Accordingly, the neurological injury can be treated or prevented by scavenging the free radicals. To scavenge free radicals, the cerium oxide nanoparticles can be administered either before or after the occurrence of stroke. While it would be preferable to administer the cerium oxide nanoparticles before the occurrence of stroke in order to minimize free radical formation, it is also beneficial to administer the cerium oxide nanoparticles once a stroke has occurred. For example, the cerium oxide nanoparticles can be administered immediately after a stroke, within 5, 10, or 15 minutes of a stroke, within a half hour of a stroke, within one hour after the stroke, or within 24 hours of the stroke. Even after the acute phase of neurological injury, administration of cerium oxide nanoparticles have been shown to have a beneficial effect in mitigating neurological injury resulting from stroke.

Cerium oxide nanoparticles can also be used to treat or prevent cardiovascular disease. Examples of cardiovascular disease include coronary heart disease (e.g., ischemic heart disease), cardiomyopathy, heart failure, cardiac dysrhythmias, inflammatory heart disease, and peripheral arterial disease. In particular, cerium oxide nanoparticles can be used to treat or prevent cardiovascular disease involving ischemia such as ischemic heart disease. Ischemic heart disease is characterized by a reduced blood supply of heart muscle, usually due to atherosclerosis. Signs and symptoms of ischemic heart disease include angina pectoris (chest pain on exertion, in cold weather or emotional situations), acute chest pain (i.e., heart attack) such as acute coronary syndrome, unstable angina or myocardial infarction, heart failure with associated difficulty in breathing or swelling of the extremities, and heartburn. Risk factors for ischemic heart disease include age, smoking, hypercholesterolaemia, diabetes, and hypertension.

In another embodiment, the cerium oxide nanoparticles are not taken up in any significant amount by the cells, but go into intravascular or interstitial spaces. In this embodiment, the nanoparticles can act to reduce or eliminate free radicals outside the cell. This can result in reduction of inflammation and inflammatory disorders. The cerium oxide nanoparticles can reduce inflammation systemically (throughout a subject's body) or locally (at the site of the inflammatory cells). The nanoparticles can reduce or eliminate inflammation that leads to preeclampsia or inflammation caused by wounding. This can also reduce or eliminate inflammation caused by the insertion of a medical prosthesis into the subject. Nanoparticles may be retained at particular sites, at least substantially retained for periods of time, by inclusion of the nanoparticles into compositions, such as dissolvable or porous matrices and the like.

In a further aspect, cerium oxide nanoparticles and compositions comprising cerium oxide nanoparticles are provided. The cerium oxide nanoparticles are size-limited and provided in an amount sufficient to provide one or more doses to a subject in need of, or suspected of being in need of, treatment for a disease or disorder involving free radicals. Compositions may comprise cerium oxide particles of the invention along with one or more other substances, which are typically substances that are biologically tolerable in that they may be exposed to living cells without killing the cells. In embodiments, the other substances are pharmaceutically acceptable substances. As used herein, "pharmaceutically acceptable substance" is intended to include solvents, coatings, antibacterial and antifungal agents, and any other ingredient that is biologically tolerable. Examples of such carriers include, but are not limited to, water, buffered saline, dextrose solution, human serum albumin, liposomes, and hydrogels. The use of such media and agents for pharmaceutically active substances is well known in the art, and thus further examples and methods of incorporating each into compositions at effective levels need not be discussed here.

Certain aspects of the invention provide for the use of cerium oxide nanoparticles in the treatment of diseases and disorders associated with free radicals, such as oxygen free radicals, or mitochondrial dysfunction. The use is in particular for in vivo therapeutic or prophylactic methods of protecting cells from free radical damage. Certain other aspects of the invention provide for the use of cerium oxide nanoparticles in the preparation of compositions for medical use, such as pharmaceutical or therapeutic compositions. In general, use of the particles is in combining them with other substances to make medicinal compositions.

Another aspect of the invention provides a container containing cerium oxide nanoparticles. In general, a container according to the invention contains a sufficient amount of size-limited cerium oxide nanoparticles made by a method other than a sol-gel method to provide at least one dose of cerium oxide to a subject suffering from, or at risk of suffering from, a disease or disorder involving free radicals, such as oxygen radicals. For example, the container may contain sufficient cerium oxide nanoparticles and, optionally, one or more other biologically tolerable substance, for one dose to a human or non-human animal subject. In certain embodiments, the container is provided in a package with one or more other containers and/or with one or more articles of manufacture or devices having use in delivery of substances to subjects (e.g., syringes, needles, antiseptic swabs, sterile saline solution). In some embodiments, kits comprising one or more containers are provided.

Regardless of whether provided alone, as part of a composition, or as part of a kit, the cerium oxide nanoparticles may be provided in any suitable physical form. Thus, they may be provided as dry particles or as part of a liquid composition. When part of a liquid composition, the composition typically will comprise water or an aqueous buffer, such as phosphate buffered saline (PBS) or other salt buffers. In general, it is preferred that the liquid composition be suitable for introduction into a living organism or for contact with a living cell without causing deleterious effects, such as cell toxicity. It is to be understood that this general preference permits inclusion of toxic components in the liquid composition as long as those components, when exposed to a living cell upon exposure to the cell, are present in a non-toxic form or at non-toxic levels. In embodiments where dry nanoparticles are administered, the nanoparticles may be in a purified state or may be in a composition comprising one or more other component. It is preferred that the other component(s) be non-toxic or, if toxic, present in an amount that, when administered, is not toxic to the cell or subject as a whole. Examples of non-toxic components include, but are not limited to, salts (e.g., sodium salts such as sodium phosphate or sodium chloride); sugars (e.g., glucose, sucrose); preservatives; and antibiotics, anti-inflammatories, albumin, lipids, or other drugs. The vehicle of delivery may be in the form of an oral solution, gel, tablet, capsule, powder, suppository, infusible, lozenge, cream, salve, inhalant, or injection.

Typically, the particles or composition comprising the particles will be sterile or will have been sterilized prior to administration to a subject or other use. The particles may be sterilized using any suitable technique known in the art, including, but not limited to, heat sterilization, filtration, and irradiation. Thus, in embodiments, the method of the invention further comprises providing sterile or sterilized cerium oxide nanoparticles, or further comprises sterilizing the nanoparticles prior to administering them to a subject.

The invention provides compositions comprising cerium oxide nanoparticles. The compositions can comprise a pharmaceutically suitable carrier, a nutritional supplement, or a dietary supplement. While not being so limited, typically the compositions comprise one or more other substances other than the nanoparticles, where the other substances are biologically tolerable (i.e., non-toxic or present in an amount that is non-toxic). Examples of such substances are well known to those of skill in the art and include, without limitation, sugars, salts, lipids, drugs, excipients, carriers, flavorants, fillers, binders, gums, colorants, water, buffers, detergents, biologically active compounds, and the like.

The present invention also provides kits. In general, the kits comprise cerium oxide nanoparticles in an amount sufficient to treat at least one patient at least one time to reduce or eliminate free radicals that can cause cell, tissue, or organ damage. Typically, the nanoparticles of the kit will be supplied in one or more container, each container containing a sufficient amount of nanoparticles for at least one dosing of the patient. The kits can comprise other components, such as some or all of the components necessary to practice a method of the invention. For example, in embodiments of the kit, albumin is included, either as a separate component or as part of a composition comprising the nanoparticles. The albumin is provided to lessen the amount or use of disruption of the nanoparticles, for example by sonication at 5-20 Hz for 2 minutes, that can sometimes be needed to provide certain formulations for delivery. The kits may contain a syringe for administering a dose of the nanoparticles. The kits may also comprise filters for sterilization of the particles prior to delivery; however, it is preferred that the particles be sterilized prior to packaging in the kits, or the entire kit be sterilized after all components are packaged. It may likewise contain sterile water or buffer for rehydration or reconstitution of dry nanoparticles, prior to administration of the particles to a patient. In embodiments, multiple doses of nanoparticles are provided in the kit, either all in a single container (e.g., a vial) or distributed among two or more containers. As the invention contemplates administering or delivering (used synonymously herein) of nanoparticles in liposomes, kits according to the invention may comprise liposomes, particularly liposomes loaded with the nanoparticles.

The following examples are included for purposes of illustration and are not intended to limit the scope of the invention.

EXAMPLES

Example 1

Evaluation of CeONP Treatment of Stroke Using a Tissue Culture Model

Given that cellular damage in human ischemic stroke arises from oxidative stress and free radical production, as well as mitochondrial dysfunction, we propose that CeONP may be used to prevent and treat neuronal dysfunction and motor deficits associated with stroke.

In Vitro Studies

We first investigated the efficacy of CeONP in treatment of stroke using a tissue culture model. In human ischemic stroke, blockade of an artery in the brain deprives a specific area of the brain of blood flow. This results in deprivation of oxygen for respiration and glucose for energy. Hence, tissue culture models for ischemic stroke involve subjecting cultured brain cells to an anoxic environment devoid of glucose and other sugars utilized to produce energy.

Methods:

We utilized a well-established in vitro tissue culture model for stroke in which cells grown in culture are deprived of oxygen and glucose (oxygen/glucose deprivation, OGD). (S M Jones et al., J. Neurosci. Methods, 199, 241-248, 2011). For these studies, mixed organotypic brain cell cultures containing neurons, astrocytes and microglia were prepared as we have previously described (Zhang & Rzigalinski, Science 274, 1921-1923, 1997). Cultures were either pretreated with CeONP or treated with CeONP 15 minutes or 1 hr after OGD, as indicated in the figures. For pretreatment studies, cultures were treated with 100 nM CeONP on day 5 in vitro. Organotypic cultures were allowed 48 hrs to take up the nanoparticles, and the medium was changed after 48 hrs. We have previously shown that cells readily take up CeONP, and retain it in the cytoplasm or mitochondria for up to 2 months, possibly longer (Rzigalinski et al., Biological Nanoparticles for Cell Engineering—A Radical Concept. In Nanotechnologies for Life Sciences, C. Kumar, editor, Wiley & Sons, 2006). For post-OGD treatment, cultures were treated with CeONP either 15 minutes or 1 hour after OGD.

On day 15 in vitro, cultures were subjected to OGD using an anaerobic chamber. Prior to use, the chamber was purged with nitrogen and filled with 90% $N_2$/10% $CO_2$. To assure lack of oxygen in the chamber, oxygen levels were monitored with a gas sensor, and were maintained at 0% for the duration of OGD. Just prior to exposure of cell cultures to OGD, cells were washed and placed in OGD medium without glucose, glutamine, or antibiotics. The OGD medium used was previously bubbled with $N_2$ for 30 minutes to remove any dissolved $O_2$, and equilibrated in the anaerobic chamber overnight prior to use.

After placement of cells in OGD medium, the cultures were sealed in the anaerobic chamber and maintained at 37° C. for 30, 60 or 90 minutes. After OGD, cultures were removed and placed in their normal culture medium (Dulbecco's Minimal Essential Medium with fetal calf serum) and cultured at 37° C. for 24 hrs. Controls (shams) were manipulated in the same manner, but were not exposed to OGD.

Assessment of Neuronal Damage: Propidium iodide (PrI) was used to assess neuronal damage. PrI is a dye that is excluded from healthy cells with intact membranes. As cells are damaged or begin to die, holes appear in the cell membrane that allow entry of PrI to the intracellular space, where the dye stains the nuclei a bright orange. PrI stained nuclei are then counted under a fluorescent microscope. PrI uptake in the neuronal layer of cells is determined by adjusting focal plane (neurons are the upper layer of cells, growing on top of astrocytes) and cell morphology. PrI data are expressed and the number of injured cells per mg of protein. To assure that cell loss did not occur during the post-OGD period, total protein in the medium and in the cellular layer was assessed. There was no increase in medium protein during the 24 hr post-OGD period, and no decrease in total protein in the attached cellular layer, indicating that cell loss through detachment had not occurred.

Intracellular Free Calcium ($[Ca^{2+}]i$). $[Ca^{2+}]_i$ was measured as we have previously described, using Fura-2 microspectrophotometery (Rzigalinski et al, J. Biol. Chem. 274, 175-182, 1999) and selective labeling of neurons (Weber, Rzigalinski, et al, J. Biol. Chem. 276, 1800-1807, 2001). Normal uninjured neurons maintain basal levels of $[Ca^{2+}]_i$ within a very tight range, from 80-105 nM. As neurons are damaged and mitochondrial function destroyed, ion gradients are dismantled and basal $[Ca^{2+}]_i$ rises, activating many cellular autodestructive functions that ultimately result in cell demise over time. Therefore, basal $[Ca^{2+}]_i$ was determined at 24 hrs post-OGD. Additionally, since our cultures are prepared from the cortex, glutamate is a major neurotransmitter in this area of the brain. After OGD and other forms of brain injury, excitotoxicity is often observed. Excitotoxicity is characterized by and excessive and aberrant rise in $[Ca^{2+}]_i$ in response to a neurotransmitter stimulus. This excessive rise in $[Ca^{2+}]_i$ is hypothesized to result from excessive glutamate release by neurons, as well as the inability of the neuron to maintain ionic gradients within the normal range. To assess excitotoxicity and neuronal signaling, we exposed cultures to a 100 μM glutamate stimulus, and recorded the change in $[Ca^{2+}]_i$.

Results

CeONP protect neurons from cell damage associated with OGD. As shown in FIG. 1, sham controls had very little uptake of PrI, indicative of healthy neurons in a normoxic environment (first set of bars). After OGD (second set of bars) we see a dramatic increase in injured neurons after 30, 60, and 90 minutes of OGD. Pretreatment of cultures with CeONP on day 5 in vitro significantly reduced neuronal damage at all levels of OGD. These results suggest that CeONP may be an effective pretreatment for prevention of neuronal death associated with OGD and/or stroke.

Figure 2:
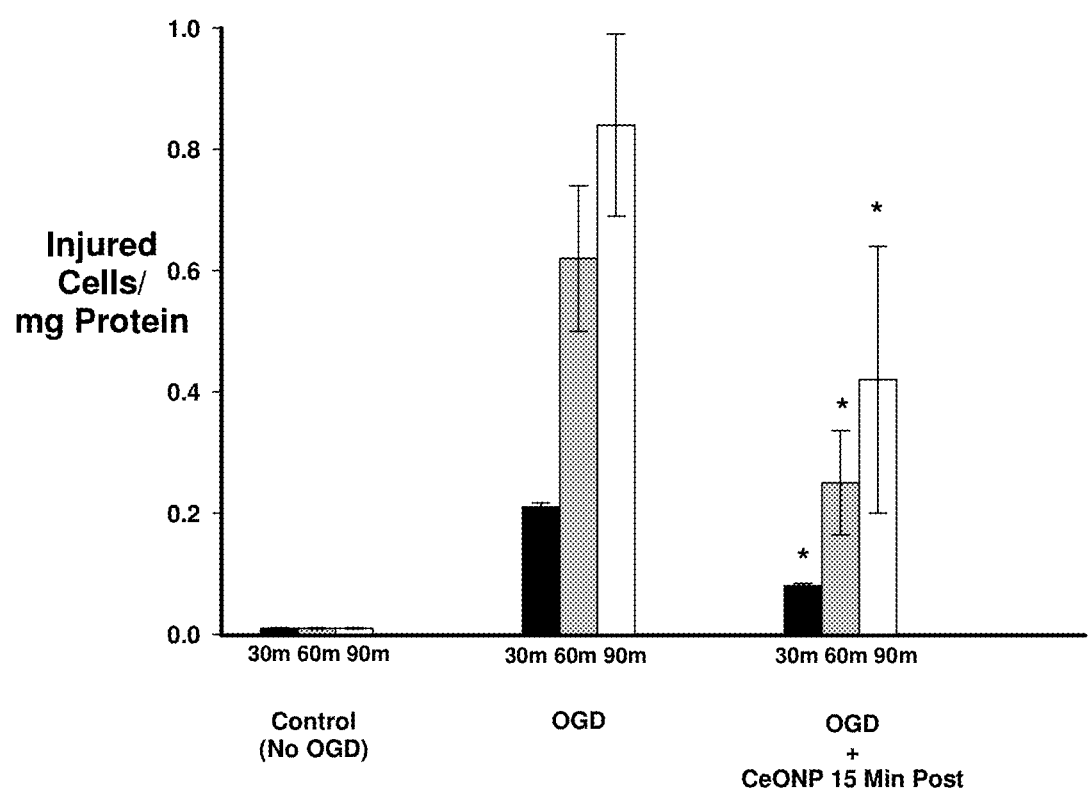
FIG. 2 provides a bar graph showing Cerium Oxide Nanoparticles promote cell survival when delivered 15 minutes after oxygen/glucose deprivation. Mixed organotypic brain cell cultures (15 days old) were exposed to oxygen/glucose deprivation for 30, 60, or 90 minutes as indicated in the figure. After oxygen/glucose deprivation, cells were returned to normal culture conditions, in medium containing 100 nM cerium oxide nanoparticles. Twenty four hours later, cell death/damage was measured by uptake of Propidium iodide, expressed on the Y axis as "injured cells per mg of protein". *Significantly different from OGD, P<0.01.
Figure 3:
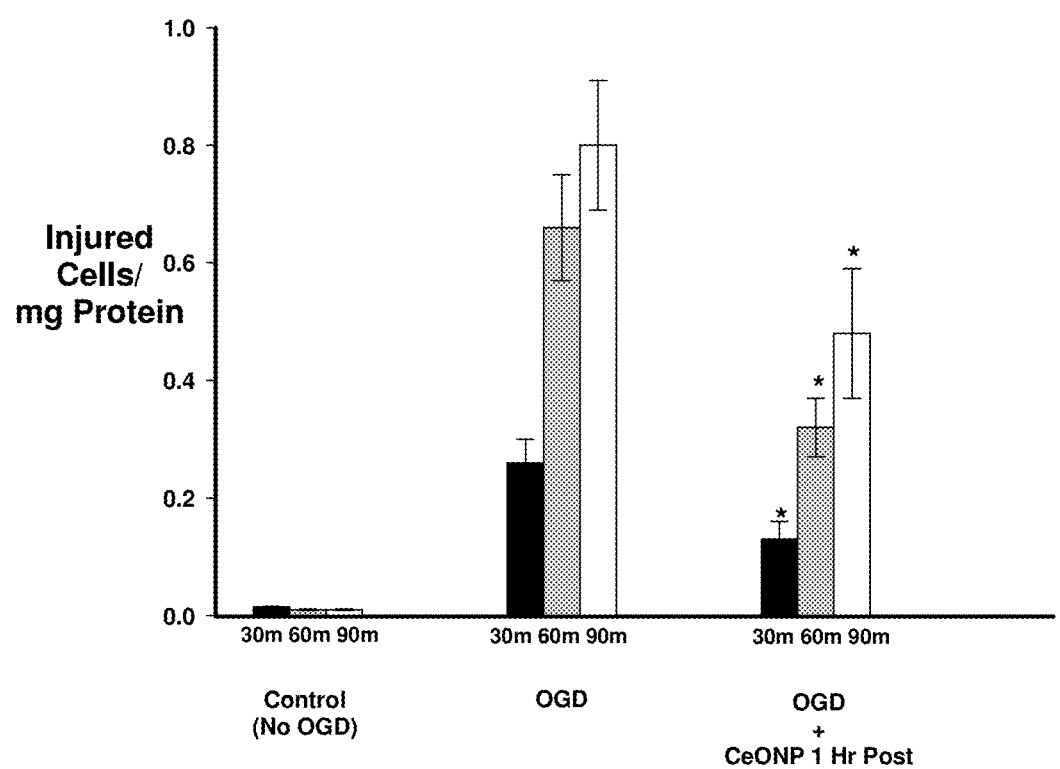
FIG. 3 provides a bar graph showing Cerium Oxide Nanoparticles promote cell survival when delivered 1 hour after oxygen/glucose deprivation. Mixed organotypic brain cell cultures (15 days old) were exposed to oxygen/glucose deprivation for 30, 60, or 90 minutes as indicated in the figure. After oxygen/glucose deprivation, cells were returned to normal culture conditions. One hour after oxygen/glucose deprivation, 100 nM cerium oxide nanoparticles were added to the cultures. Twenty four hours later, cell death/damage was measured by uptake of Propidium iodide, expressed on the Y axis as "injured cells per mg of protein". *Significantly different from OGD, P<0.01.

CeONP promote cell survival when delivered after OGD. In FIGS. 2 and 3, we see the same low cellular damage rate in our sham controls. As expected, there is a dramatic increase in cell damage at all time points of OGD. In FIG. 2, third set of bars, cultures received 100 nM CeONP 15 minutes after the end of OGD. A single dose of CeONP significantly decreased cell damage after all levels of OGD, from 52-46%.

Similar results were observed when CeONP were delivered 1 hour after OGD (FIG. 3), with significant levels of neuroprotection observed at all levels of OGD, even when CeONP were delivered 1 hr after OGD. Taken together, these results suggest that CeONP may be an effective post-stroke treatment to reduce neuronal damage.

Figure 4:
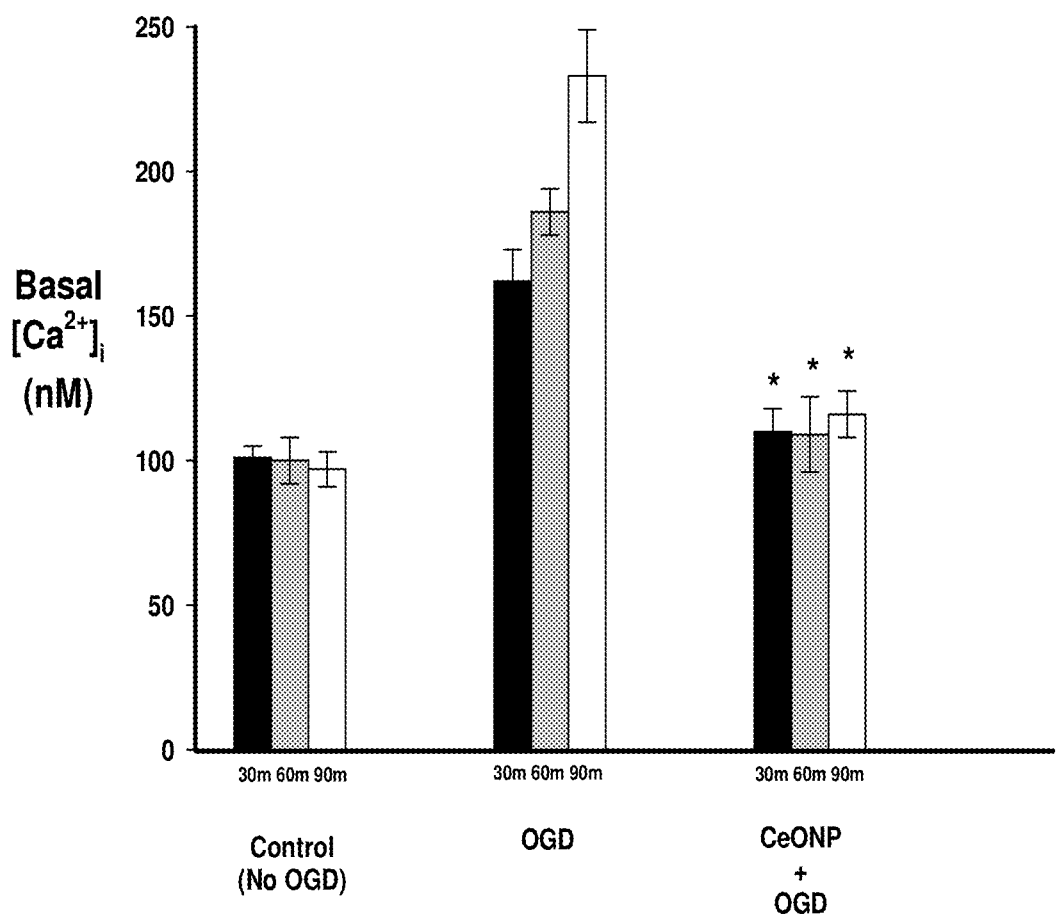
FIG. 4 provides a bar graph showing Cerium Oxide Nanoparticles preserve basal $[Ca^{2+}]i$ when delivered before oxygen/glucose deprivation. Mixed organotypic brain cell cultures were treated with 100 nM cerium oxide nanoparticles on day 5 in vitro. On day 15, cultures were exposed to oxygen/glucose deprivation for 30, 60, or 90 minutes as indicated in the figure. After oxygen/glucose deprivation, cells were returned to normal culture conditions. Twenty four hours later, cells were loaded with Fura-2 and basal $[Ca^{2+}]i$ was determined microspectrophotometrically. *Significantly different from OGD, P<0.01.

CeONP preserve basal $[Ca^{2+}]_i$ when delivered before OGD. As discussed earlier, basal Cai in neurons is maintained within tight control, to keep normal cellular systems functioning optimally and to promote neuronal signaling and communication. As shown in FIG. 4, sham controls had basal $[Ca^{2+}]_i$ levels of between 90-105 nM, consistent with our prior observations (leftmost set of bars). Twenty four hrs after various 30, 60, and 90 min OGD, basal $[Ca^{2+}]_i$ was dramatically and significantly elevated (middle set of bars). Elevation of $[Ca^{2+}]_i$ to these levels is known to activate cellular autodestructive functions, damage mitochondria, and blunt neuronal signaling; often resulting in cell death. However in cultures pretreated with CeONP, the rise in basal $[Ca^{2+}]_i$ after OGD was significantly blunted, with near-normal basal $[Ca^{2+}]_i$ levels being maintained. These results suggest that CeONP pretreatment may preserve normal basal calcium levels in neurons after stroke.

Figure 5:
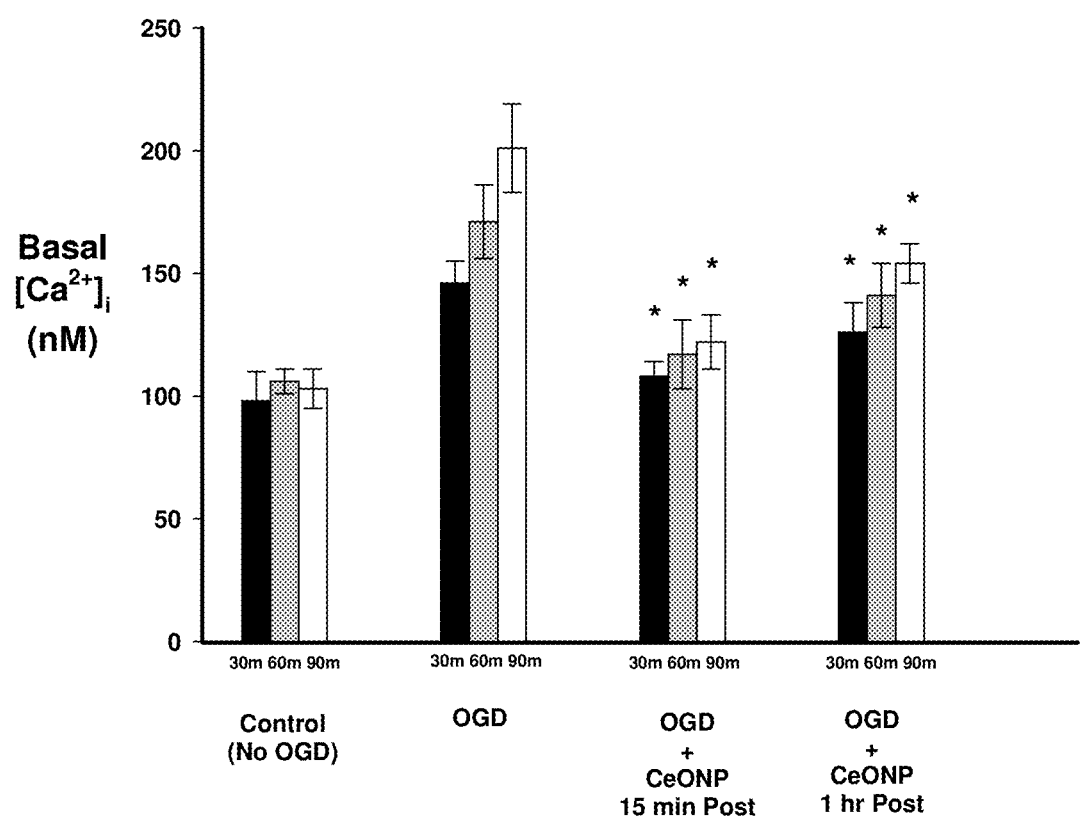
FIG. 5 provides a bar graph showing Cerium Oxide Nanoparticles preserve basal $[Ca^{2+}]i$ when delivered after oxygen/glucose deprivation. Mixed organotypic brain cell cultures (15 days old) were exposed to oxygen/glucose deprivation for 30, 60, or 90 minutes as indicated in the figure. After oxygen/glucose deprivation, cells were returned to normal culture conditions and treated with 100 nM cerium oxide nanoparticles at either 15 minutes post-deprivation, or 1 hour post-deprivation. Twenty four hours later, cells were loaded with Fura-2 and basal $[Ca^{2+}]i$ was determined microspectrophotometrically. *Significantly different from OGD, P<0.01.

CeONP preserve basal $[Ca^{2+}]i$ when delivered after OGD. Next, we determined whether delivery of CeONP after OGD would still preserve basal $[Ca^{2+}]_i$ levels. As shown in FIG. 5, delivery of 100 nM CeONP either 15 minutes or 1 hr after OGD still resulted in a significant decrease in basal $[Ca^{2+}]_i$ to levels much closer to that observed in normal cells (FIG. 5). Take together, these findings indicate that CeONP may be an effective pharmaceutical to block the elevations in basal $[Ca^{2+}]_i$ that may induced neuronal damage after stroke.

Figure 6:
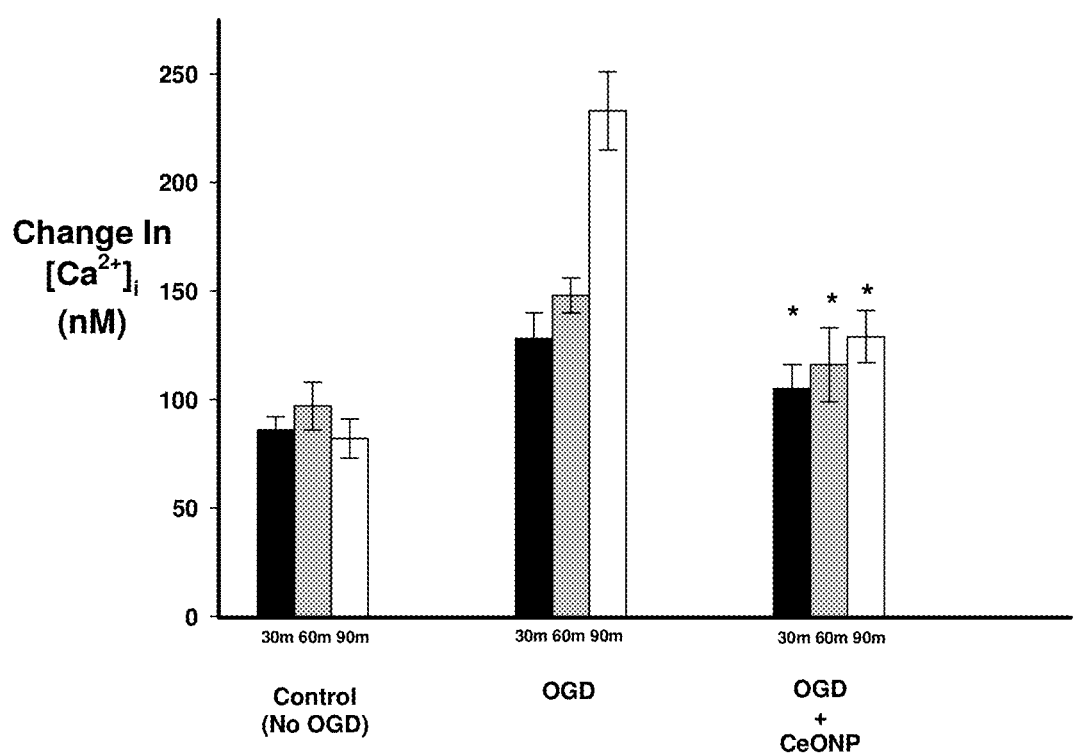
FIG. 6 provides a bar graph showing Cerium Oxide Nanoparticles preserve near-normal glutamate signaling when delivered prior to oxygen/glucose deprivation. Mixed organotypic cultures were treated with 100 nM cerium oxide nanoparticles on day 5 in vitro. On day 15, cultures were exposed to oxygen/glucose deprivation for 30, 60, or 90 minutes as indicated in the figure. After oxygen/glucose deprivation, cells were returned to normal culture conditions. Twenty four hours later, cell cells were loaded with Fura-2. The change in $[Ca^{2+}]i$ in response to a 100 mM glutamate stimulus was measured. *Significantly different from OGD, P<0.01.
Figure 7:
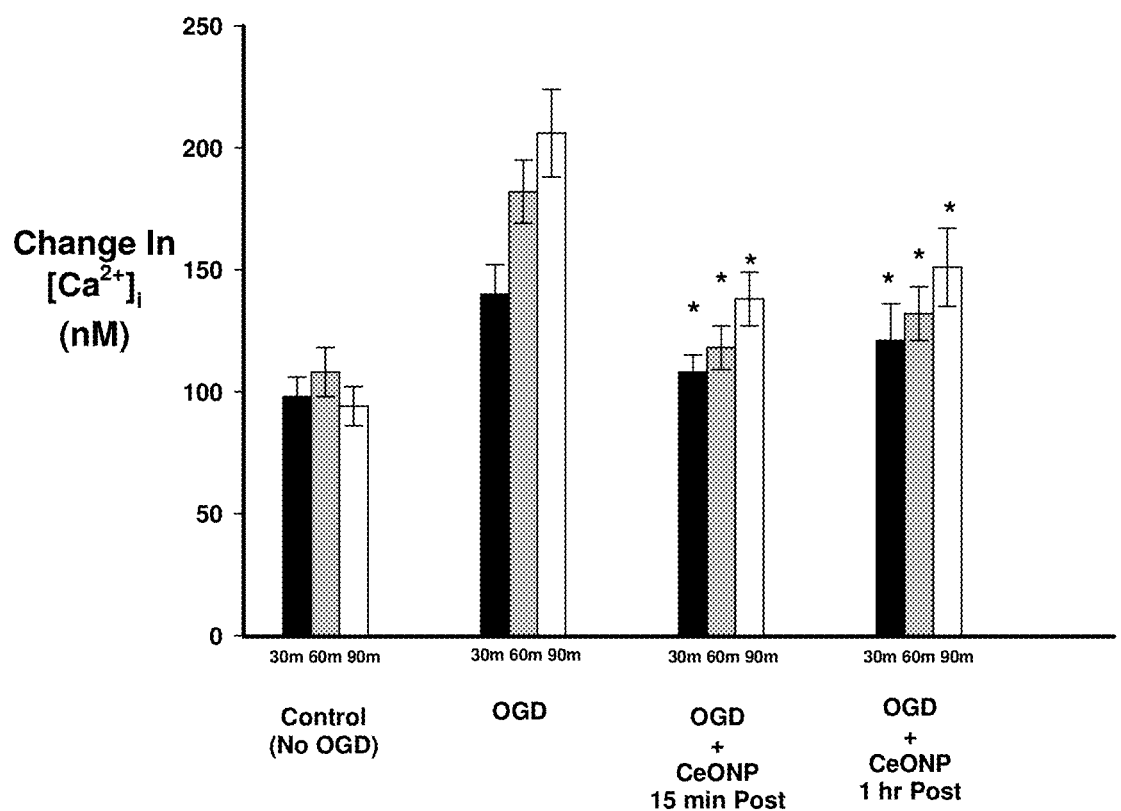
FIG. 7 provides a bar graph showing Cerium Oxide Nanoparticles preserve glutamate-stimulated $[Ca^{2+}]i$ when delivered after oxygen/glucose deprivation. Mixed organotypic cultures (15 days old) were exposed to oxygen/glucose deprivation for 30, 60, or 90 minutes as indicated in the figure. After oxygen/glucose deprivation, cells were returned to normal culture conditions and treated with 100 nM cerium oxide nanoparticles at either 15 minutes post-deprivation, or 1 hour post-deprivation. Twenty four hours later, cell cells were loaded with Fura-2. The change in $[Ca^{2+}]i$ in response to a 100 mM glutamate stimulus was measured. *Significantly different from OGD, P<0.01.

Cerium Oxide Nanoparticles preserve near-normal glutamate signaling when delivered prior to oxygen/glucose deprivation. We next examined how CeONP might improve neuronal calcium signaling in response to neurotransmitters after OGD, using the primary excitatory neurotransmitter, glutamate. As shown in FIG. 6, sham controls responded to 100 mM glutamate with a change in $[Ca^{2+}]_i$ (above basal) from between 80-100 nM, similar to our previously published reports (first set of bars). Twenty four hrs after OGD, the response to glutamate was significantly enhanced, achieving levels of 130-240 nM, consistent with what we have previously observed with excitotoxicity. However in neurons pretreated with CeONP, the glutamate stimulated $[Ca^{2+}]_i$ elevations were significantly blunted, from 110-138 nM (right set of bars). These results demonstrate that pretreatment with CeONP may preserve neuronal signaling after stroke, and have the potential to decrease stroke-associated dysfunction. In FIG. 7, CeONP were delivered 15 min or 1 hr after OGD. Once again, we see that the dramatic rise in glutamate-stimulated $[Ca^{2+}]_i$ elevation was blunted in neurons treated with CeONP.

Taken together with observations of basal $[Ca^{2+}]_i$ our results suggest that CeONP may be used to prevent neuronal damage observed in stroke, may be used to prevent $[Ca^{2+}]_i$ dysregulation induced by stroke, and may be used to treat neurons after stroke, to block neuronal damage/death, calcium dysregulation, and excitotoxicity Example 2

Evaluation of CeONP Treatment of Stroke Using a *Drosophila* Animal Model

The tissue culture studies described in Example 1 strongly suggest that CeONP may be utilized as prevention and treatment for neurological deficits produced by stroke. Next, we tested our hypothesis in an animal model, *Drosophila melanogaster*, the fruit fly. See Rodriquez et al., J. Exptl. Biol. 215, 4157-4165, 2012.

*Drosophila* is used as a model for many human diseases and neurodegenerative disorders, including Alzheimer's disease, Parkinson's disease, Huntington's disease, stroke, and numerous others. Although it is an insect, utility of *Drosophila* models arises from the fact that large numbers can be easily obtained and culture is relatively inexpensive, compared to mammalian models. The entire *Drosophila* genenome has been sequenced, making genetic studies readily available. Further, animal care and use laws consider *Drosophila* a viable alternative to immediate use of mammalian models.

For this stroke study, we utilized a well-characterized model for stroke, oxygen-glucose deprivation. Reports in the literature demonstrate that *Drosophila* undergo neuronal damage and loss via OGD and have histological neuronal damage similar to that observed in humans. Additionally, functional deficits are also similar to those observed in humans, including loss of learning, memory and motor function.

Methods

One day old male and female flies were collected upon enclosure from the pupa and cultured on commercial fly food (Jazz mix) supplemented with CeONP at 1, 100 and 200 μM doses. Control group food was supplemented with vehicle (0.01% docusate sodium) as we have previously described. Groups were separated into male and female, and there were 100 male and female flies per group.

Flies were cultured for 14 days in standard vials at 25° C. with 50% humidity, and were turned over into new food vials every 2 days. On day 15, flies were placed into empty vials and subjected to OGD. OGD was produced by placing the flies in a tightly sealed gas tent. Flies were placed in the tent which was then purged of all air and filled with nitrogen. Lack of oxygen in the tent was measured with a sensor placed inside the tent. Within 15 minutes of beginning the oxygen removal and nitrogen replacement, flies ceased activity and were immobilized on the bottom of the vial. Flies remained in this environment for 2.5 hrs.

After the stroke period, flies were removed from the tent and placed in standard vials containing their respective food groups, and allowed to recover. In the male cohort, there was a 10% loss due to death, with a 20% loss in the female cohort, within 3 days of stroke. No significant differences in immediate death were noted between the groups.

Since loss of motor function is a common problem associated with stroke, motor function in *Drosophila* was measured by assessing the negative geotactic response. Negative geotaxis is the ability of the flies to climb the walls of the vial to various heights. For these experiments, flies were placed in an empty vial and gently tapped to the bottom of the vial. Climbing to 3 heights was then determined, 3 cm, 5.5 cm, and 8 cm. Flies were given 10 seconds to achieve each respective height goal. The percentage of flies achieving each height goal was determined. Negative geotaxis was measured in all groups on day 14 (1 day prior to stroke) and at 2, 6, 14, and 36 days after stroke.

Results

Male Fly Data

Figure 8:
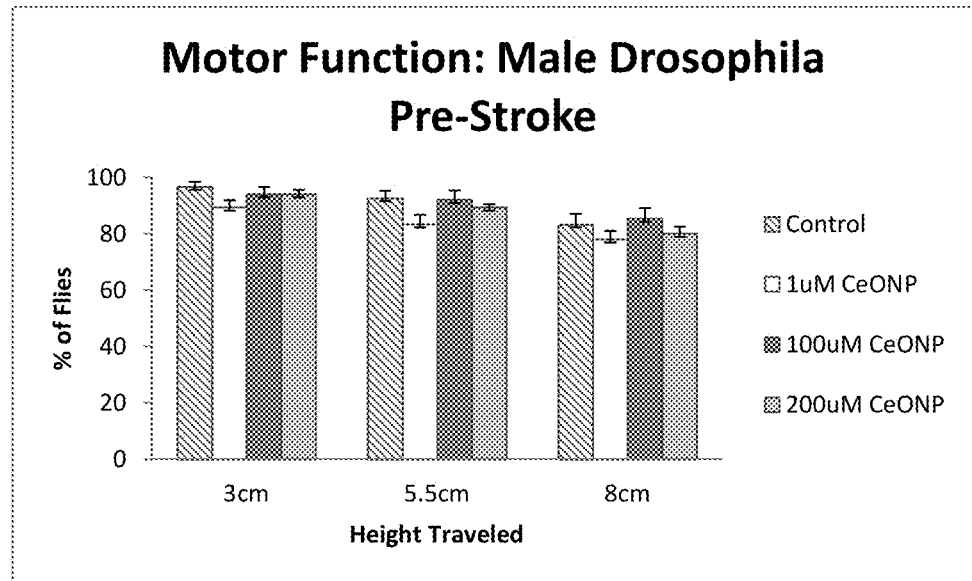
FIG. 8 provides a bar graph showing Motor Function in Normal *Drosophila*. Flies were fed standard food (Jazz Mix) or food containing the indicated concentrations of cerium oxide nanoparticles for 14 days. On day 14, pre-stroke motor function was assessed by measuring negative geotaxis, the ability of flies to climb the walls of an empty vial to 3, 5.5, and 8 cm, in 10 seconds. Data is expressed as the percentage of flies achieving each height goal in the required time.

Negative geotaxis data for all male fly groups prior to delivery of stroke is shown in FIG. 8. There was no significant difference between food groups (i.e. normal vs CeONP).

Figure 9:
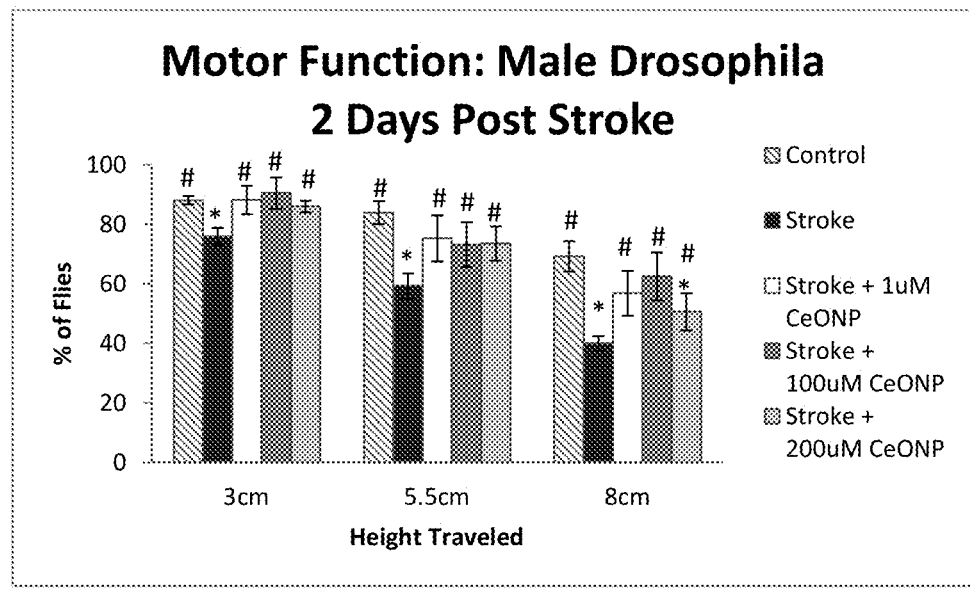
FIG. 9 provides a bar graph showing CeONP-treated male flies had normal motor function after stroke. Flies were fed as described in FIG. 8. On day 15 flies were exposed to anoxia for 2.5 hrs, followed by return to their respective food group. Two days after stroke, motor function was assessed by negative geotaxis. Note that flies fed standard food and exposed to stroke had significantly decreased motor function as compared to normal flies. CeONP preserved the negative geotactic response in stroked flies, to levels equivalent to normal controls at the 3 and 5.5 cm goal heights. At the 8 cm height, CeONP significantly improved performance as compared to stroked flies. *Sig. from all control, P<0.01; # Sig. from stroke, P<0.01.

In FIG. 9, flies were assessed for motor function using negative geotaxis, at 2 days after stroke. We see that stroke (black bar) decreased the negative geotactic response at all levels of climbing (3, 5.5, and 8 cm). However in flies treated with 1-200 μM CeONP, the negative geotactic response was preserved to the level seen in normal controls for the 3 and 5.5 cm goals. For the 8 cm goal, all CeONP groups showed significantly better performance than stroked flies, with the 100 mM dose showing performance equivalent to untreated controls.

Figure 10:
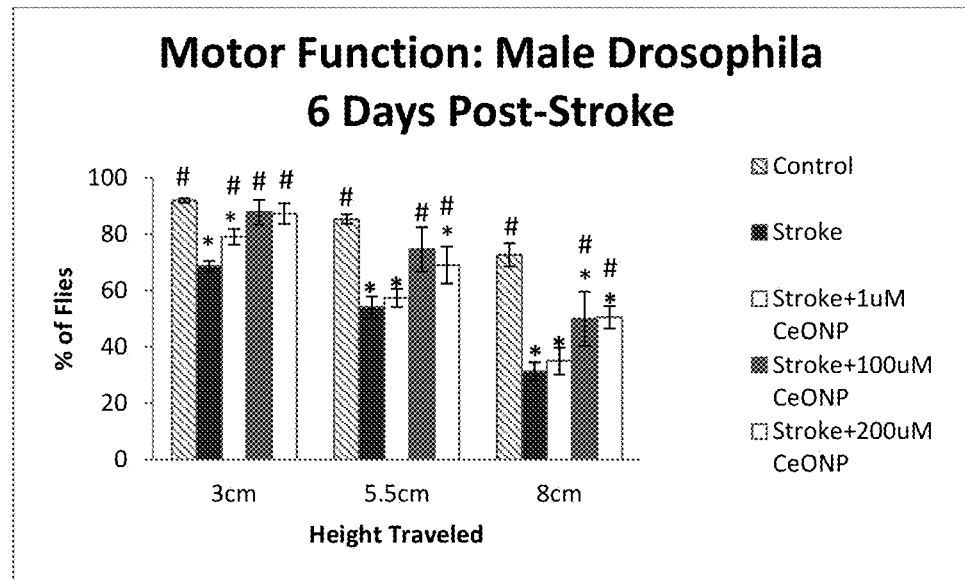
FIG. 10 provides a bar graph showing CeONP-treated male flies have improved motor function 6 days after stroke. Flies were fed and exposed to anoxia as described in FIG. 9. Six days after stroke, motor function was assessed by negative geotaxis. Flies fed standard food and exposed to stroke continued to have significantly decreased motor function at all heights compared to normal controls. However flies fed 100 and 200 μM CeONP continued to show improved motor function as compared to stroked flies. *Sig. from control, P<0.01; g #Sig from stroke, P<0.01.

At 6 days post-stroke (FIG. 10), untreated, stroked flies continued to show depressed geotactic responses at all height goals. Flies fed the lowest (1 μM) dose of CeONP (white bars) also showed a decline in motor function, scoring similar to untreated stroked flies. However flies fed 100 and 200 μM CeONP continued to show improved motor function which was not different from controls at 3 cm goal heights.

Figure 11:
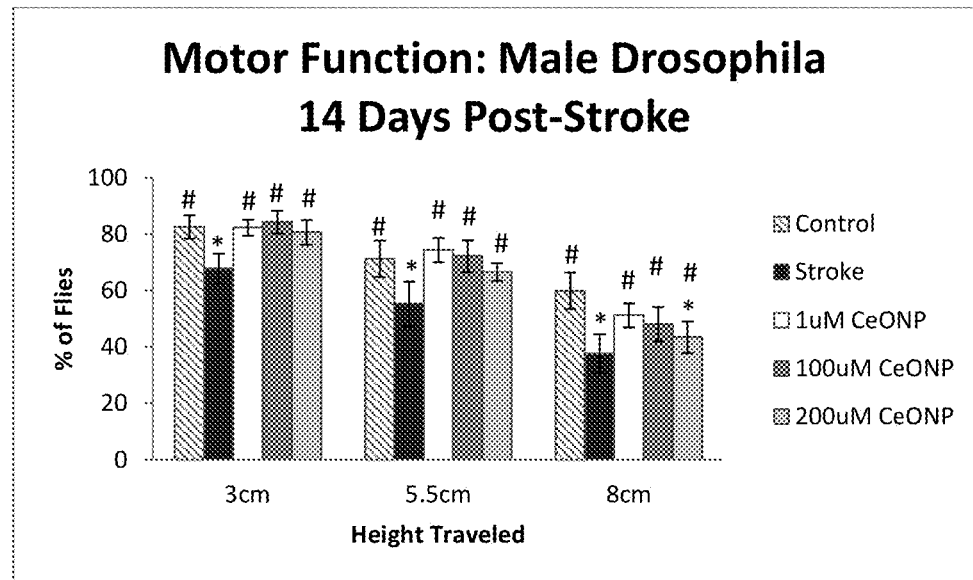
FIG. 11 provides a bar graph showing CeONP-treated male flies have improved motor function 14 days after stroke. Flies were fed and exposed to anoxia as described in FIG. 9. Fourteen days after stroke, motor function was assessed by negative geotaxis. Flies fed standard food and exposed to stroke continued to have significantly decreased motor function at all goal heights compared to normal controls. CeONP preserved the negative geotactic response in stroked flies, to levels equivalent to normal controls, with the exception of the 200 µM food group at the 8 cm height. *Sig. from control, P<0.01; #Sig from stroke, P<0.01.
Figure 12:
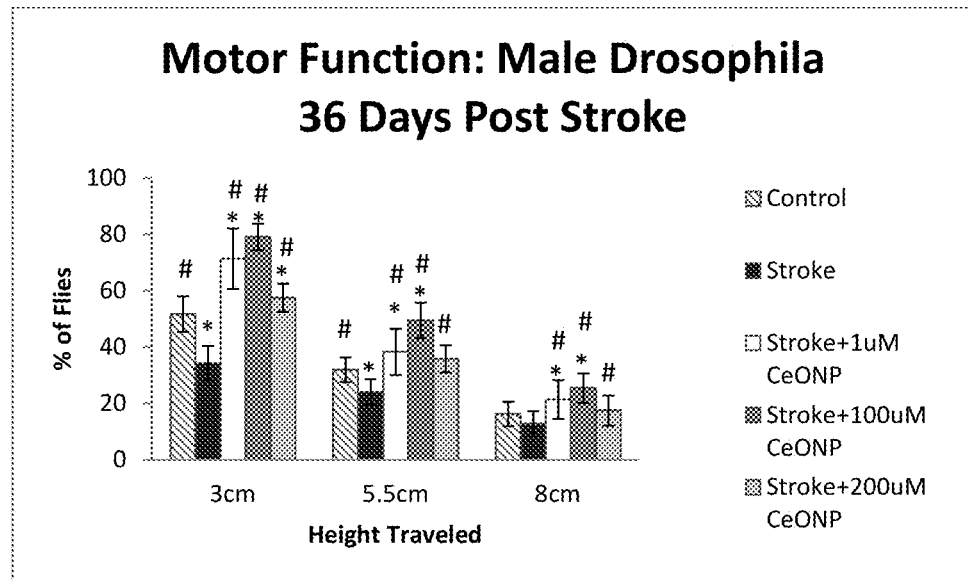
FIG. 12 provides a bar graph showing CeONP-treated male flies have improved motor function 36 days after stroke. Flies were fed and exposed to anoxia as described in FIG. 9. Thirty six days after stroke, motor function was assessed by negative geotaxis. Controls (unstroked) flies showed decreased motor function as compared to their motor function on days 2-14. This is typical, as the flies are now reaching the end of their life span (flies are now 54 days old with an average lifespan of 58-60 days). Flies fed standard food and exposed to stroke continued to have significantly decreased motor function at all goal heights compared to normal controls. CeONP preserved the negative geotactic response in stroked flies at all goal heights. Additionally, flies fed CeONP had improved motor function, as compared to unstroked controls (with the exception of the 200 mM food group at 8 cm. *Sig. from control, P<0.01; #Sig from stroke, P<0.01.

At 14 days post-stroke (FIG. 11), motor function remained depressed in untreated stroked flies at all height goals. However in flies treated with 1-200 μM CeONP, motor function returned to levels that were equal to that of non-stroked control male flies, with the exception of the highest goal (8 cm) for the flies fed the highest dose (200 µM) CeNOP.

At 36 days after stroke, motor function was assessed again. Controls (unstroked) flies showed decreased motor function as compared to their motor function on days 2-14. This is typical, as the flies are now reaching the end of their life span (flies are now 54 days old with and have an average lifespan of 58-60 days). Flies fed standard food and exposed to stroke continued to have significantly decreased motor function at all goal heights compared to normal controls. CeONP preserved the negative geotactic response in stroked flies at all goal heights. Interestingly, flies fed CeONP had improved motor function, as compared to unstroked controls (with the exception of the 200 µM food group at 8 cm), suggesting that CeONP may also improve motor function with aging.

Female Fly Data

Figure 13:
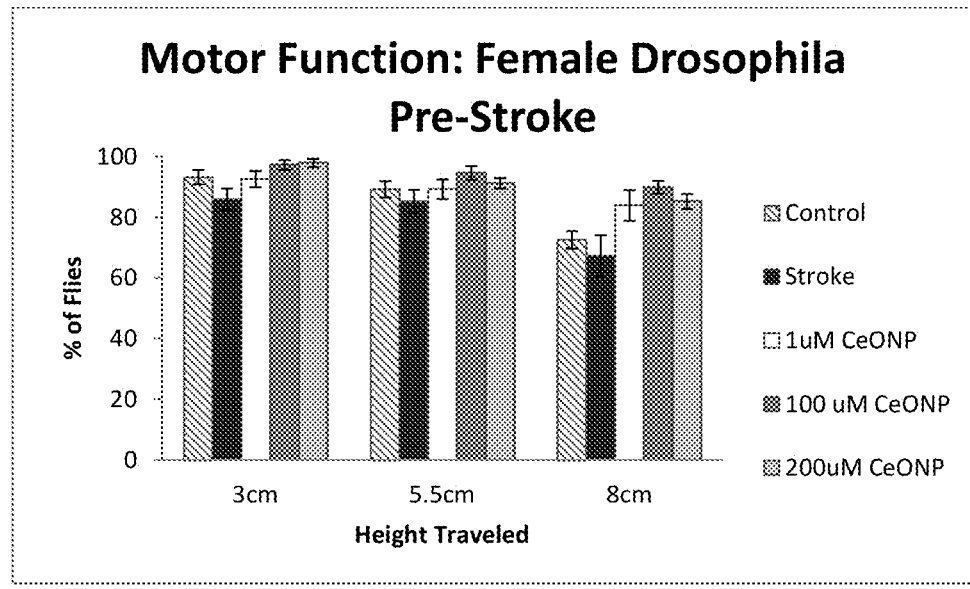
FIG. 13 provides a bar graph showing Motor Function in Normal Female *Drosophila*. Flies were fed standard food (Jazz Mix) or food containing the indicated concentrations of cerium oxide nanoparticles for 14 days. On day 14, motor function was assessed by measuring negative geotaxis, the ability of flies to climb to 3, 5.5, and 8 cm in a 10 second minute period. Data is expressed as the percentage of flies achieving each height goal in the required time.

Negative geotaxis data for all female fly groups prior to delivery of stroke is shown in FIG. 13. There was no significant difference between food groups (i.e. normal vs CeONP).

Figure 14:
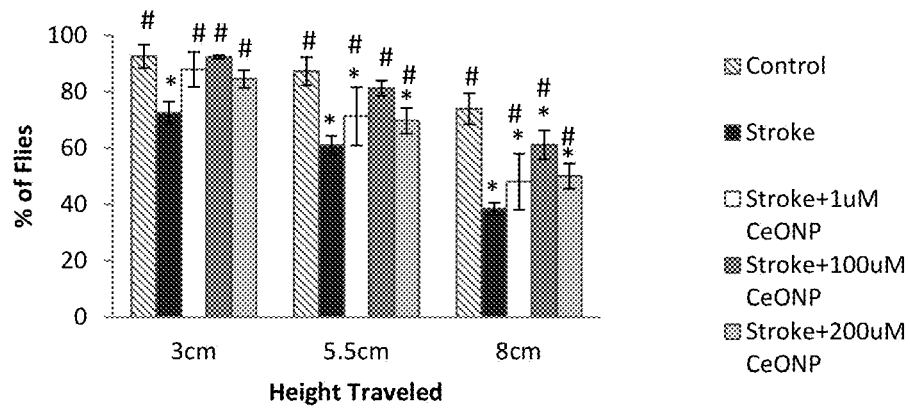
FIG. 14 provides a bar graph showing CeONP-treated female flies had increased motor function after stroke. Flies were fed as described in FIG. 8. On day 15 flies were exposed to anoxia for 2.5 hrs, followed by return to their respective food group. Two days after stroke, motor function was assessed by negative geotaxis. Note that flies fed standard food and exposed to stroke had significantly decreased motor function as compared to normal flies. CeONP significantly improved the negative geotactic response in stroked female flies, to levels equivalent to normal controls at the 3 cm climbing height. *Sig. from control, P<0.01; # Sig. from stroke, P<0.01.

Two days after stroke, females showed a decline in motor function, as shown in FIG. 14. Compared to males, the female decline in motor function was somewhat more severe for all climbing goal heights. Flies treated with CeONP showed significant improvement in motor function for all climbing goal heights. Climbing heights for the 3 and 5.5 cm goals in stroked flies treated with 100 and 200 µM CeONP were similar to unstroked controls.

Figure 15:
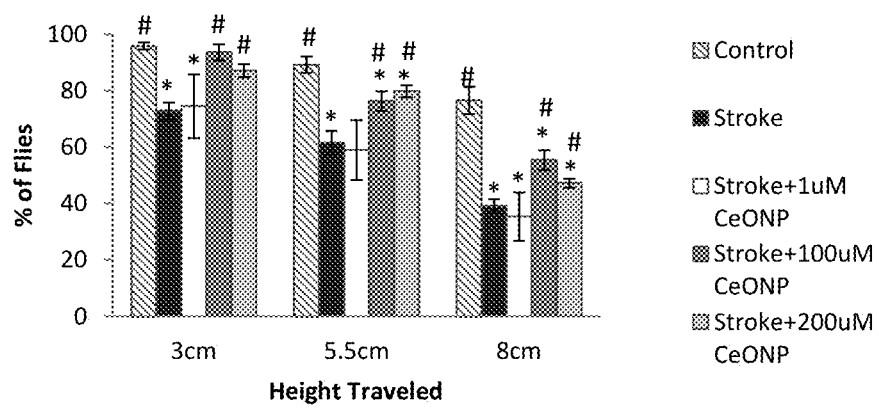
FIG. 15 provides a bar graph showing CeONP-treated female flies have improved motor function 6 days after stroke. Flies were fed and exposed to anoxia as described in FIG. 9. Six days after stroke, motor function was assessed by negative geotaxis. Females fed standard food and exposed to stroke continued to have significantly decreased motor function at all heights. Females treated with 100 and 200 µM CeONP showed improved motor function at all goal heights, as compared to stroked flies, with climbing to the 3 cm height equivalent to unstroked controls. *Sig. from control, P<0.01; #Sig from stroke, P<0.01.

Six days after stroke females fed standard food and exposed to stroke continued to have significantly decreased motor function at all goal heights (FIG. 15). Females treated with 100 and 200 µM CeONP showed significantly improved motor function at all goal heights. Climbing to the 3 cm height was equivalent to that observed in unstroked controls. The 1 mm dose, again showing a trend toward improved motor function, did not show significantly greater improvement as compared to stroked flies.

Figure 16:
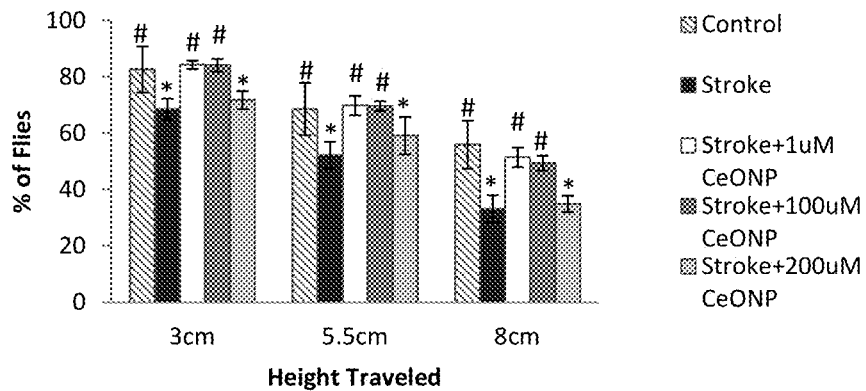
FIG. 16 provides a bar graph showing CeONP-treated female flies have improved motor function 14 days after stroke. Flies were fed and exposed to anoxia as described in FIG. 9. Fourteen days after stroke, motor function was assessed by negative geotaxis. Flies fed standard food and exposed to stroke continued to have significantly decreased motor function at all goal heights compared to normal controls. CeONP preserved the negative geotactic response in stroked flies at the 1 and 100 µM doses, to levels equivalent to normal controls. *Sig. from control, P<0.01; #Sig from stroke, P<0.01.

Fourteen days after stroke, motor function was again assessed by negative geotaxis, as shown in FIG. 16. Note that controls show a small decline in motor function as compared to that observed on day 14 (just prior to stroke). Again, this is typical with aging flies, as these groups are now 29 days old (approximately midlife). Flies fed standard food and exposed to stroke continued to have significantly decreased motor function at all goal heights compared to normal controls. CeONP preserved motor function in stroked flies at the 1 and 100 µM doses, to levels equivalent to normal controls.

Figure 17:
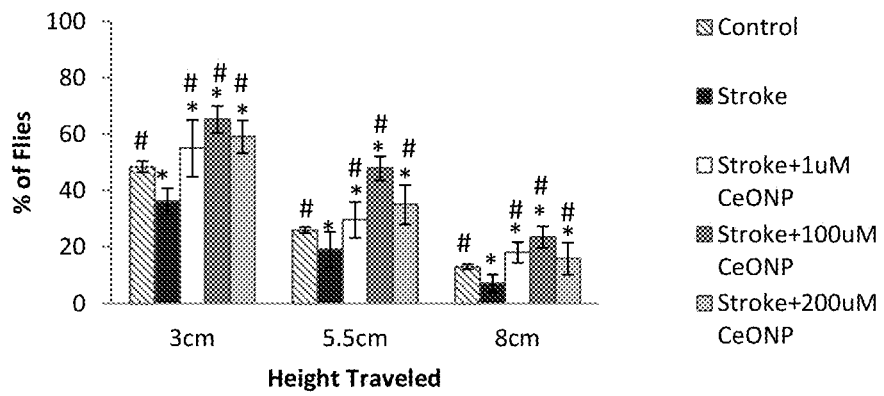
FIG. 17 provides a bar graph showing CeONP-treated female flies have improved motor function 36 days after stroke. Flies were fed and exposed to anoxia as described in FIG. 9. Thirty six days after stroke, motor function was assessed by negative geotaxis. Controls (unstroked) flies continued to show decreased motor function as compared to their motor function on days 2-14. This is typical, as the flies are now reaching the end of their life span (flies are now 54 days old with an average lifespan of 58-60 days). Flies fed standard food and exposed to stroke continued to have significantly decreased motor function at all goal heights compared to normal controls. All doses of CeONP preserved the negative geotactic response in stroked flies at all goal heights, to levels that were greater than control (unstroked) flies. *Sig. from control, P<0.01; #Sig from stroke, P<0.01.

Thirty six days after stroke (FIG. 17), controls (unstroked) flies continued to show decreased motor function as compared to their motor function on days 2-14. Again, this is typical, as the flies are now reaching the end of their life span (flies are now 54 days old with an average lifespan of 58-60 days). Flies fed standard food and exposed to stroke continued to have significantly decreased motor function at all goal heights compared to normal controls. All doses of CeONP preserved the negative geotactic response in stroked flies at all goal heights. Interestingly, the geotactic response was preserved to levels that significantly exceeded normal, unstroked flies. This again suggests that CeONP may blunt the normal decline in motor function seen with aging.

CONCLUSIONS

Female *Drosophila* are more susceptible to deleterious effects of stroke/OGD. Male and female flies fed with CeONP (1-200 mM) prior to and after stroke had dramatically improved motor function, equivalent to controls (unstroked) in some cases.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating neurological injury in a subject who has suffered a stroke, comprising administering a therapeutically effective amount of a composition consisting of non-agglomerated cerium oxide nanoparticles and a pharmaceutically suitable carrier to the subject.

2. The method of claim 1, wherein the cerium oxide nanoparticles are administered within one hour after the stroke.

3. The method of claim 1, wherein the cerium oxide nanoparticles are administered within 15 minutes after the stroke.

4. The method of claim 1, wherein the cerium oxide nanoparticles are administered more than once to the subject.

5. The method of claim 1, wherein the subject is human.

6. The method of claim 1, wherein the nanoparticles have a size from 10 nm to 20 nm.

7. The method of claim 1, wherein a 0.005-5 micrograms per gram weight dose of cerium oxide nanoparticles is provided.

8. The method of claim 1, wherein the subject is exhibiting impaired motor function.

9. A method of lessening the severity of injury from a stroke in a subject comprising administering a therapeutically effective amount of a composition consisting of non-agglomerated cerium oxide nanoparticles and a pharmaceutically suitable carrier to the subject prior to occurrence of the stroke.

10. The method of claim 9, wherein the subject has one or more risk factors associated with the occurrence of a stroke.

11. The method of claim 9, wherein the cerium oxide nanoparticles are administered more than once to the subject.

12. The method of claim 9, wherein the subject is human.

13. The method of claim 9, wherein having a size ranging from 10 nm to 20 nm.

14. The method of claim 9, wherein a 0.005-5 micrograms per gram weight dose of cerium oxide nanoparticles is provided.

* * * * *